US011124800B2

(12) United States Patent
Lorence et al.

(10) Patent No.: US 11,124,800 B2
(45) Date of Patent: Sep. 21, 2021

(54) METHOD OF IMPROVING CHLOROPLAST FUNCTION AND INCREASING SEED YIELD

(71) Applicant: Arkansas State University—Jonesboro, State University, AR (US)

(72) Inventors: Argelia Lorence, Jonesboro, AR (US); Jessica Patricia Yactayo-Chang, Jonesboro, AR (US)

(73) Assignee: Arkansas State University—Jonesboro, State University (AR)

( * ) Notice: Subject to any disclaimer, the term of this patent is extended or adjusted under 35 U.S.C. 154(b) by 22 days.

(21) Appl. No.: 15/829,788

(22) Filed: Dec. 1, 2017

(65) Prior Publication Data

US 2018/0245093 A1  Aug. 30, 2018

Related U.S. Application Data

(60) Provisional application No. 62/428,775, filed on Dec. 1, 2016.

(51) Int. Cl.
*C12N 15/82* (2006.01)
*C12N 9/18* (2006.01)

(52) U.S. Cl.
CPC .......... *C12N 15/8261* (2013.01); *C12N 9/18* (2013.01); *C12N 15/8243* (2013.01); *C12N 15/8269* (2013.01); *C12Y 301/01017* (2013.01); *Y02A 40/146* (2018.01)

(58) Field of Classification Search
None
See application file for complete search history.

(56) References Cited

U.S. PATENT DOCUMENTS 7,033,781 B1 * 4/2006 Short ................... C12N 15/102
435/6.16
2011/0162107 A1 * 6/2011 Inze ..................... C07K 14/415
800/290

FOREIGN PATENT DOCUMENTS

WO    2004035798   4/2004
WO    2006104503   10/2006

OTHER PUBLICATIONS

Brooks et al. A thioredoxin-like/β-propeller protein maintains the efficiency of light harvesting in Arabidopsis. Proc Natl Acad Sci U S A. Jul. 16, 2013;110(29):E2733-40. 1305443110. Epub Jul. 1, 2013. (Year: 2013).*
Gallie. L-ascorbic Acid: a multifunctional molecule supporting plant growth and development. Scientifica (Cairo). 2013;2013:795964. Epub Jan. 17, 2013. Review. (Year: 2013).*
Kondo et al. Senescence marker protein 30 functions as gluconolactonase in L-ascorbic acid biosynthesis, and its knockout mice are prone to scurvy. Proc Natl Acad Sci U S A. Apr. 11, 2006; 103(15):5723-8. Epub Apr. 3, 2006. (Year: 2006).*
Farrell. The Regulation of Gene Expression in Plants and Animals. Chapter 1 pp. 1-38 In Regulation of Gene Expression in Plants, Edited by Carole L. Bassett., 2007, Springer. (Year: 2007).*
Earley et al. Gateway-compatible vectors for plant functional genomics and proteomics. Plant J. Feb. 2006;45(4):616-29. (Year: 2006).*
Carrington et al. Cap-independent enhancement of translation by a plant potyvirus 51 nontranslated region. J Virol. Apr. 1990;64(4): 1590-7. (Year: 1990).*
Lorence et al., "myo-Inositol oxygenase offers a possible entry point into plant ascorbate biosynthesis," Plant Physiology, 2004, 134, pp. 1200-1205.
Aizawa S, et al. (2013). Structural basis of the ?-lactone-ring formation in ascorbic acid biosynthesis by the senescence marker protein-30/gluconolactonase. PLoS ONE 8(1): e53706.
Barth C, et al (2004). The timing of senescence and response to pathogens is altered in the ascorbate deficient Arabidopsis mutant vitamin c-1. Plant Physiol. 134:1784-1792.
Belisle, M. "Closing and characterization of two putative glucuronolactonases from Arabidopsis thaliana involved in ascorbate degradation." Worcester Polytechnic Institute Digital WPI (2007) 1-30.
Bulley, Sean M., et al. "Gene expression studies in kiwifruit and gene over-expression in Arabidopsis indicates that GDP-L-galactose guanyltransferase is a major control point of vitamin C biosynthesis." Journal of Experimental Botany 60.3 (2009): 765-778.
Chen CN, et al (2008). The first crystal structure of gluconolactonase important in the glucose secondary metabolic pathways. J. Mol. Biol. 384:604-614.
Conklin PL et al (2004). Ascorbic acid, a familiar small molecule intertwined in the response of plants to ozone, pathogens, and the onset of senescence. Plant Cell Environ. 27:959-970.
Conklin PL, et al (1996). Environmental stress sensitivity of an ascorbic acid-deficient Arabidopsis mutant. Proc Natl. Acad. Sci USA 3:9970-9974.
Constable BJ (1963). Ascorbic acid in chloroplasts. Nature 198: 483-484.
Database Geneseq "Thale cress protein repressed in E2Fa/Dpa expressing plants SeqID 1374" (2007) Retrieved from EBI accession No. GSP:ADN73479 Database Accession No. ADN73479.
Davey MW, et al (2000). Plant L-ascorbic acid: chemistry, function, metabolism, bioavailability and effects of processing. J. Sci. Food Agric. 80:825-860.

(Continued)

*Primary Examiner* — Cynthia E Collins
(74) *Attorney, Agent, or Firm* — Quarles & Brady LLP

(57) ABSTRACT

Ascorbate protects tissues against damage caused by reactive oxygen species (ROS) produced through normal metabolism or generated from stress. The inositol route to AsA involves four enzymes: myo-inositol oxygenase, glucuronate reductase, gluconolactonase (GNL), and L-gulono-1,4-lactone oxidase (GulLO). Eighteen putative GNLs were identified in *Arabidopsis*, one of which, AtGNL, is interesting because it possesses a chloroplastic signal peptide. Knockouts on this gene had lower foliar AsA and stunted growth compared to controls. The functional gene restored the phenotype of the knockouts, and those plants had higher AsA content, enhanced photosynthetic capacity, and higher seed yield.

20 Claims, 40 Drawing Sheets
Specification includes a Sequence Listing.

(56) References Cited

OTHER PUBLICATIONS

Dowdle J, et al (2007). Two genes in Arabidopsis thaliana encoding GDP-L-galactose phosphorylase are required for ascorbate biosynthesis and seedling viability. Plant J. 52:673-689.
Eckardt NA (2003). Controlling organelle positioning: a novel chloroplast movement protein. Plant Cell 15:2755-2757.
European Patent Office, Extended European Search Report for European Patent Application No. 17877368.5 dated Apr. 21, 2020.
Foyer CH et al (2003). Redox sensing and signaling associated with reactive oxygen in chloroplast, peroxisomes and mitochondria. Physiol. Plant. 119:355-364.
Foyer et al., 1983, Measurement of the ascorbate content of spinach leaf protoplasts and chloroplasts during Ilumination, Planta, 157, 239-244.
Habermann HM (2013). Light dependent oxygen metabolism of chloroplast preparation. III. Photooxidation of ascorbic acid. Plant Physiol. 26(N2):252-261.
Haroldsen V, et al (2011). Constitutively expressed DHAR and MDHAR influence fruit, but not foliar ascorbate levels in tomato. Plant Physiol. Biochem. 49:1244-1249.
Horemans et al 2000 Ascorbate function and associated transport systems in plants. Plant Physiology and Biochemistry 38(7-8):531-540.
Ishikawa T et al (2008). Recent advances in ascorbate biosynthesis and the physiological significance of ascorbate peroxidase in photosynthesizing organism. Biosci. Biatechnol. Biochem. 72:1143-1154.
Ishikawa T, et al (2006). Progress in manipulating ascorbic acid biosynthesis and accumulation in plants. Physiol. Plant. 126:343-355.
Klimyuk V, et al (2012). Production of recombinant antigens and antibodies in Nicotiana benthamiana using imagnifection' technology: GMP-compliant facilities for small- and large-scale manufacturing. Curr. Top. Microbial. Immunol. 375:127-154.
Lisko KA, et al (2013). Elevating vitamin C content via overexpression of myo-inositol oxygenase and L-gulono-1, 4-lactone oxidase in Arabidopsis leads to enhanced biomass and tolerance to abiotic stresses. In Vitro Cell Develop Biol Plant. 49:643-655.
Lorence A et al (2007). Pathway engineering of the plant vitamin C metabolic network. Applications of Plant Metabolic Engineering. R Verpoorte, AW Alfermann and TS Johnson (eds). Springer, Netherlands, 197-217.
Lorence A., et al. "Myo-inositol oxygenase offers a possible entry point into plant ascorbate biosynthesis." Plant Physiology 134.3 (2004): 1200-1205.
Mittler et al., 2004, Reactive oxygen gene network of plants, Trends in Plant Science, 9(10), 490-498.
Miyaji T, et al (2014). AtPHT4;4 is a chloroplast-localized ascorbate transporter in Arabidopsis. Nature. DOI:10.10385928.
Munné-Bosch S et al (2002). Interplay between ascorbic acid and lipophilic antioxidant defenses in chloroplasts of water-stressed Arabidopsis plants. FEBS Lett. 524:145-148.
Oelze et al 2008 Redox regulation and overreduction control in the photosynthesizing cell: complexity in redox regulatory networks. Biochim Biophys Acta 1780: 1261-1272.
Ogawa K, et al (2002). Coimmobillization of gluconolactonase with glucose oxidase for improvement in kinetic property of enzymatically induced volume collapse in ionic gels. Biomacromolecules. 3:625-631.
Pavet V, et al (2005). Ascorbic acid deficiency activates cell death and disease resistance responses in Arabidopsis. Plant Physiol. 139:1291-1303.
Pintó-Marijuan M et al (2014). Photo-oxidative stress markers as a measure of abiotic stress-induced leaf senescence: advantages and limitations. J Exp. Bot 65(14):3845-3857.
Shao HB, et al (2008). Higher plant antioxidants and redox signaling under environmental stresses. C. R. Biol. 331:433-441.
Shinagawa E, et al (2009). Solubilization, purification, and properties of membrane-bound D-glucono-s-lactone hydrolase from Gluconobacter oxydans. Biosci. Biotechnol. Biochem. 73:241-244.
Smirnoff N, et al (2001) Biosynthesis of ascorbic acid in plants: a renaissance. Annu Rev Plant Physiol Plant Mol Biol 52: 437-467.
Talla S, et al (2011). Ascorbic acid is a key participant during the interactions between chloroplasts and mitochondria to optimize photosynthesis and protect against photoinhibition. J Biosci. 36(1):163-173.
Tamaoki M, et al (2003). Light controlled expression of a gene enconding L-galactono-lactone dehydrogenase which affects ascorbate pool size in Arabidopsis thaliana. Plant Sci. 16:1111-1117.
Tarighi S, et al (2008). The PA4204 gene encodes a periplasmic gluconolactonase (PpgL) which is important for Fitness of Pseudomonas aeruginosa. Microbiology 154:2979-2990.
Tóth, S. Z., et al. "The physiological role of ascorbate as photosystem II electron donor: protection against photoinactivation in heat-stressed leaves." Plant Physiology 156.1 (2011): 382-392.

* cited by examiner

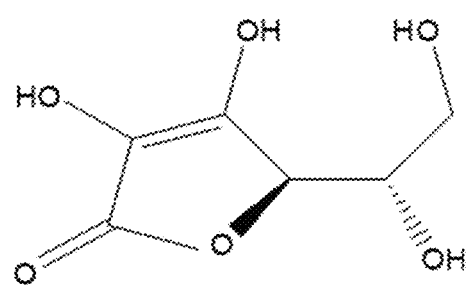
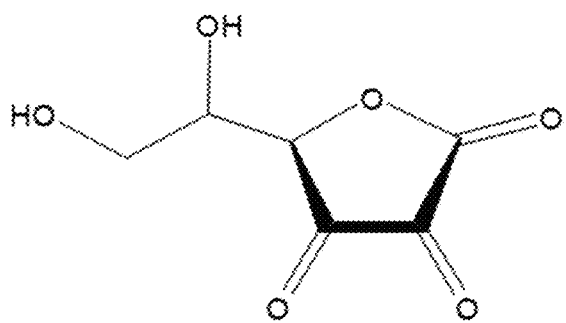
L-Ascorbic acid
Reduced form
$C_6H_8O_6$
Mol. Wt.: 176.12
Dehydroascorbic acid
Oxidized form
$C_6H_6O_6$
Mol. Wt.: 174.11
FIG. 1

| N° | Locus | Knockout | Predicted Localization | Notes |
|---|---|---|---|---|
| 1 | At1g08470 | SALK_055631 | NA | Strictosidine synthase family protein |
| 2 | At1g56500 | SALK_011623 SALK_026172 | Chloroplast | Haloacid dehalogenase-like hydrolase family |
| 3 | At1g74000 | SALK_032305 | Cell wall | Encondes a protein similar to strictosidine synthase |
| 4 | At1g74020 | SALK_001853 | Endomembrane system | Responds to JA; strictosidine synthase family protein |
| 5 | At2g01410 | SALK_147211 | Endomembrane system | Expressed protein; AsA |
| 6 | At2g16780 | SALK_001214 | NA | WD-40 repeat protein (MSI2), contains 5 WD-40 repeats (PF0400) |
| 7 | At2g24130 | SALK_025037 | Endomembrane system | Leucine-rich repeat transmembrane protein kinase, putative |
| 8 | At2g41290 | SALK_015649 | Endomembrane system | Strictosidine synthase family protein |
| 9 | At2g41300 | SALK_009989 | Endomembrane system | Strictosidine synthase family protein |
| 10 | At3g51420 | SALK_026466 | Endomembrane system | Strictosidine synthase family protein |
| 11 | At3g51430 | SALK_055182 | Endomembrane system | Strictosidine synthase |
| 12 | At3g51440 | SALK_057855 | Endomembrane system | Strictosidine synthase family protein |
| 13 | At3g51450 | SALK_124438 | Endomembrane system | Strictosidine synthase family protein |
| 14 | At3g57010 | SALK_091299 | Endomembrane system | Strictosidine synthase family protein |
| 15 | At3g57020 | NA | Endomembrane system | Strictosidine synthase family protein |
| 16 | At3g57030 | SALK_120135 | Cell wall | Strictosidine synthase family protein |
| 17 | At3g59530 | SALK_033871 | Endomembrane system | Strictosidine synthase family protein |
| 18 | At5g22020 | SALK_042799 | Endomembrane system | Strictosidine synthase family protein |

FIG. 5

A. At1g56500-HIS:pBIB-Kan
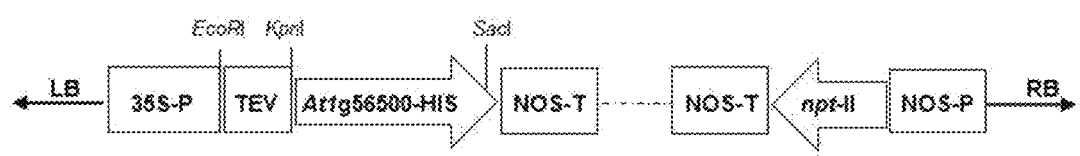
B. pAt1g56500:pCAMBIA1305.1
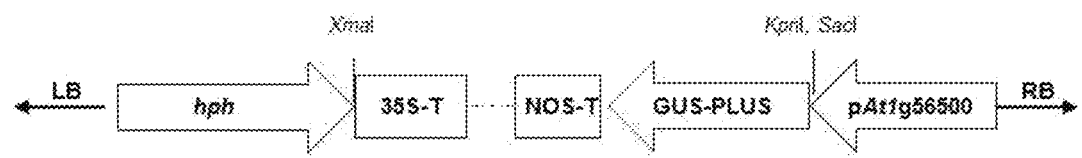
FIG. 8

| N° | Buffers | Ref |
|---|---|---|
| 1 | 50 mM sodium phosphate pH 7.2, 0.6% protease inhibitor cocktail | Lorence Laboratory |
| 2 | 50 mM sodium phosphate pH 7.2, 150 mM NaCl, 0.1% Tween-20, 0.6% protease inhibitor cocktail | Lorence Laboratory |
| 3 | 50 mM Tris-HCl pH 8.0, 0.6% protease inhibitor cocktail | Lorence Laboratory |
| 4 | 50 mM Tris, 150 mM $MgCl_2$, 10 mM sodium metabisulfite, 0.1% Tween-20, 0.6% protease inhibitor cocktail | Reichel and Beachy, 1998 |
| 5 | 50 mM MES-NaOH pH 6.0, 0.6% protease inhibitor | Lorence Laboratory |
| 6 | 75 mM sodium phosphate dibasic, 25 mM sodium phosphate monobasic, 300 mM NaCl, 10 mM sodium metabisulfite, 0.6% protease inhibitor cocktail | Lorence Laboratory |

FIG. 9

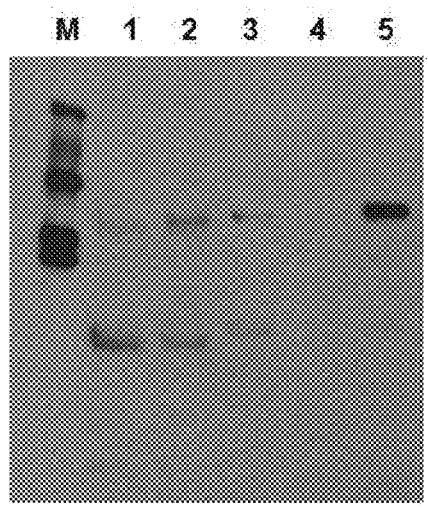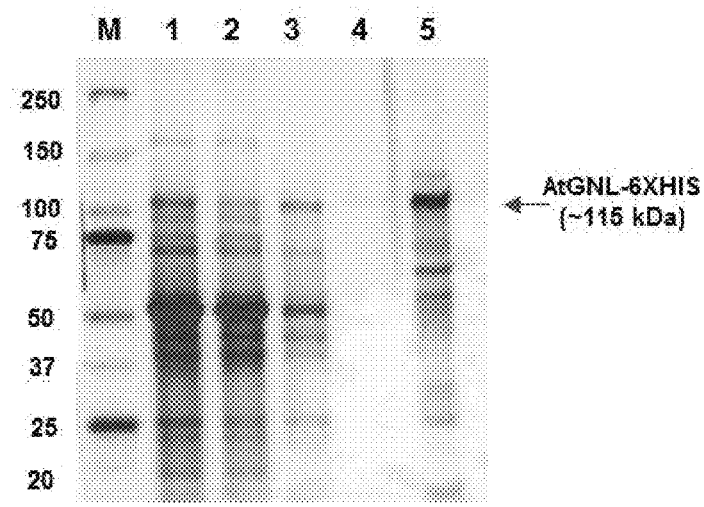
FIG. 12

| Substrate[a] | Rate[b] (%) |
|---|---|
| D-Glucono-δ-lactone | 100 |
| L-Galactono-γ-lactone | ND |
| L-Galactonic acid | ND |
| L-Gulono-γ-lactone | ND |
| L-Gulonic acid | ND |

[a]Concentration of substrate was 5 mM. [b]Enzyme activity was determined under standard reaction conditions as defined in "Materials and methods" using the lactonase activity assay, 30 μg of enzyme, and the indicated substrate. ND: no detectable enzyme activity.

FIG. 13

A. Temperature
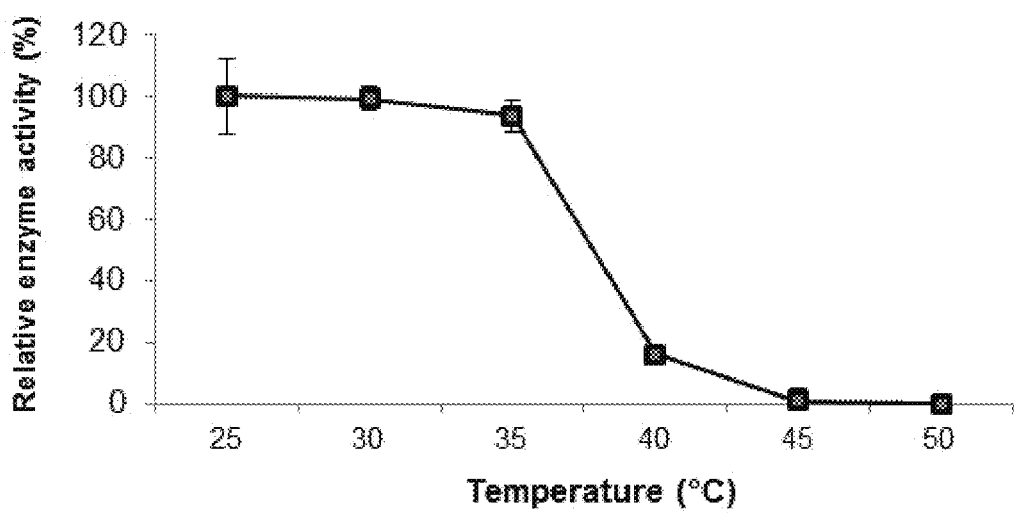
B. pH
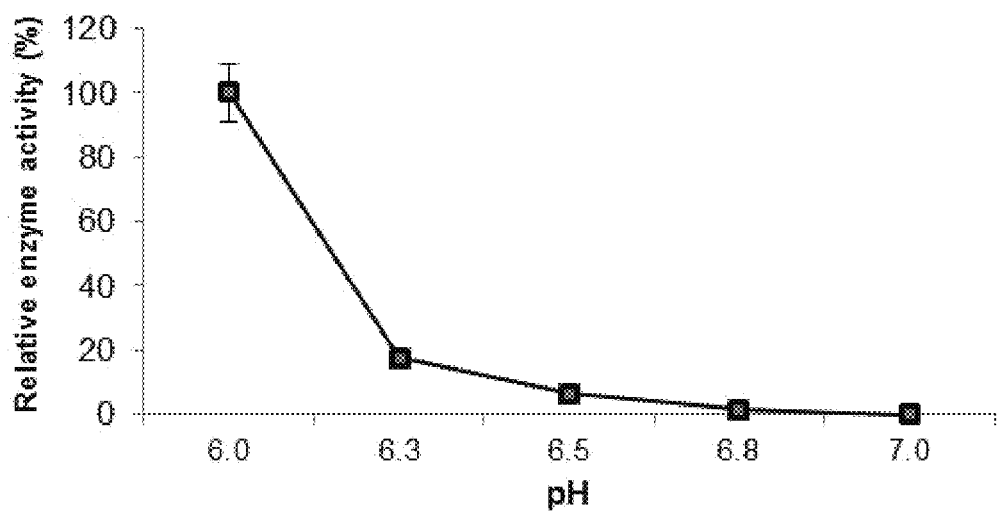
FIG. 14

A. Cofactor
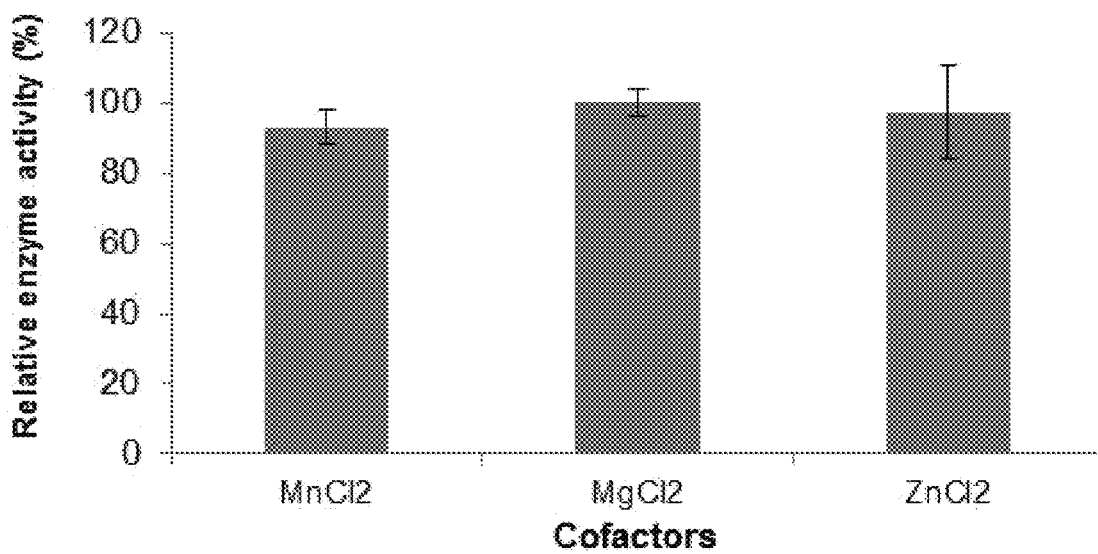
B. Substrate concentration
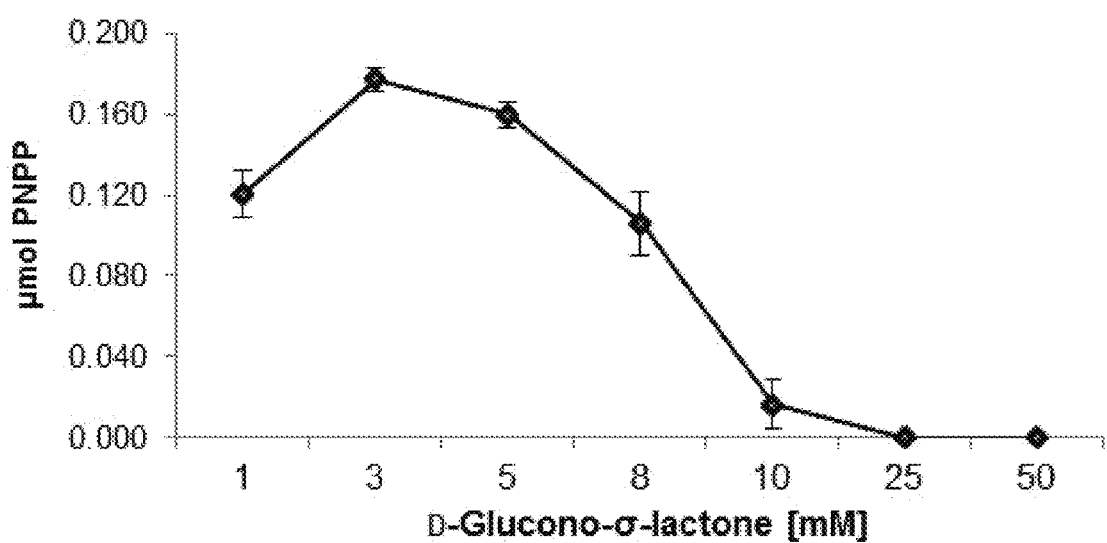
FIG. 15

A. Michaelis-Menten
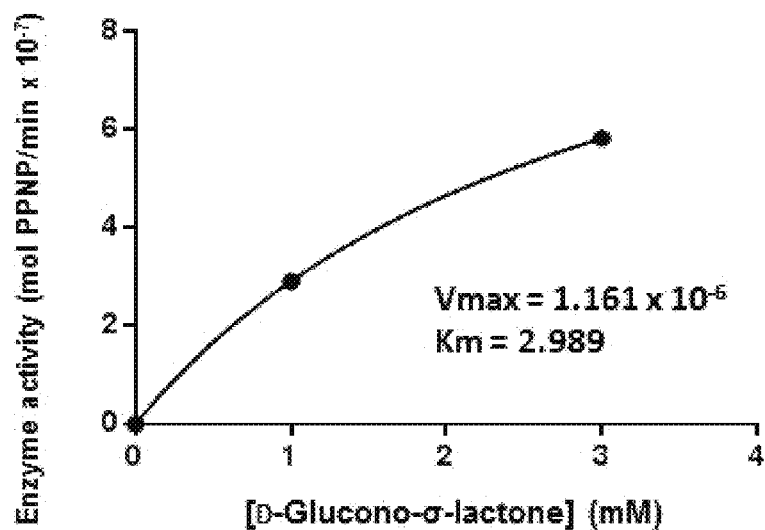
B. Double reciprocal Lineweaver-Burke
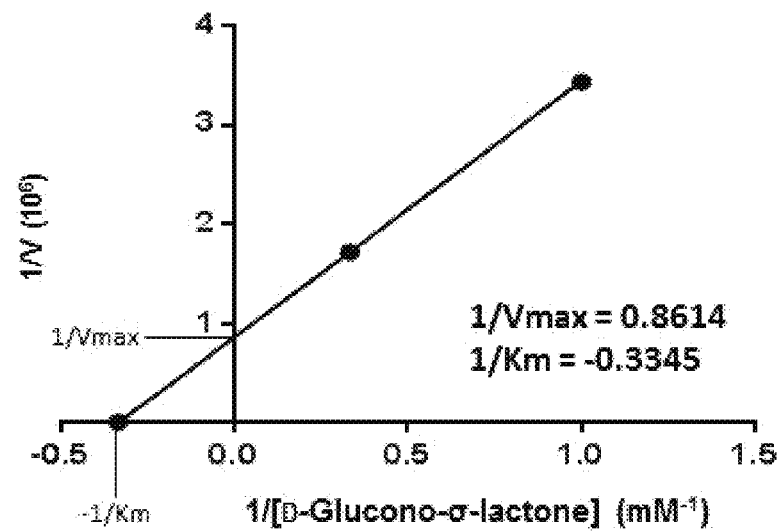
FIG. 16

| Species | pH | Cofactor | Specific activity (µmol min⁻¹ mg⁻¹ of protein) | Km (mM) | Vmax (µmol min⁻¹ mg⁻¹ of protein) | Ref |
|---|---|---|---|---|---|---|
| Arabidopsis thaliana | 6.0 | $Mn^{+2}$, $Mg^{+2}$, $Zn^{+2}$ | 10.54 | 3 | 38.7 | This work |
| Rattus novergicus | 6.4 | $Zn^{2+}$ | 9 | 9.4 | 345 | Kondo et al., 2006 |
| Euglena gracilis | 6.5 | $Zn^{2+}$ | 39 | 9.4 | 345 | Ishikawa et al., 2008 |
| Pseudomonas aeruginosa | 7.2 | not mentioned | not mentioned | not mentioned | not mentioned | Tarighi et al., 2008 |
| Xanthomonas campestri | 7.0 | $Ca^{2+}$ | not mentioned | 16.2 | 160 | Chen et al. 2009 |
| Gluconobacter oxydans | 6.0 | $Ca^{2+}$ | not mentioned | 2.5 | 25 | Shinagawa et al., 2009 |
| Homo sapiens (SMP30)* | 6.4 | $Ca^{2+}$ | 25 | not mentioned | not mentioned | Aizawa et al., 2013 |
| Mus musculus | 6.4 | $Ca^{2+}$ | 8.8 | not mentioned | not mentioned | Aizawa et al., 2013 |

*The human GNL a.k.a. senescence marker protein 30 or SMP30 is a protein whose tissue levels in the liver, kidney and lung decrease with aging.

FIG. 17

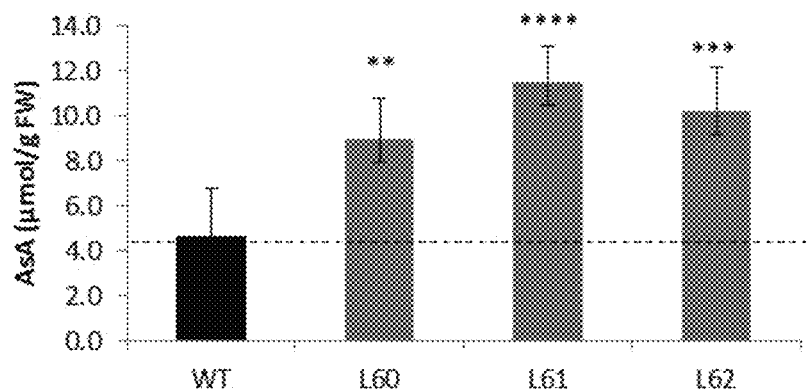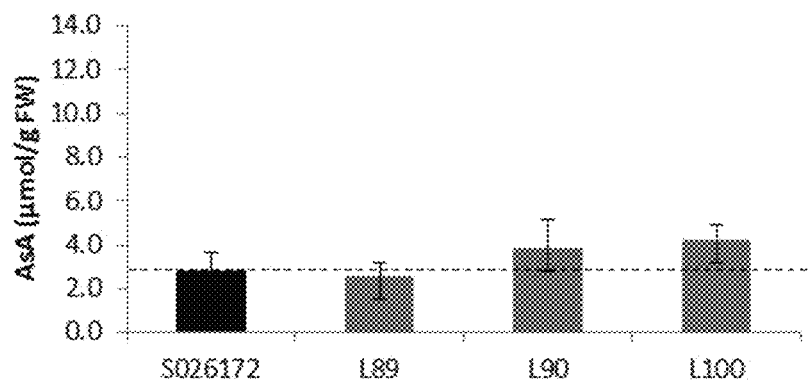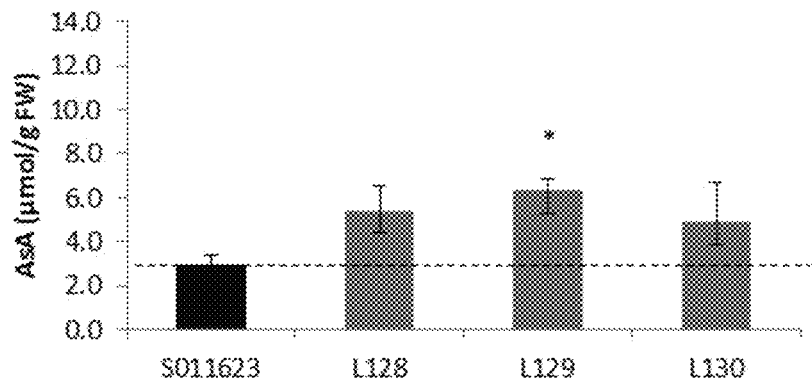
FIG. 18

A. Representative images of the phenotype of GNL knockouts, over-expresser and restored lines.
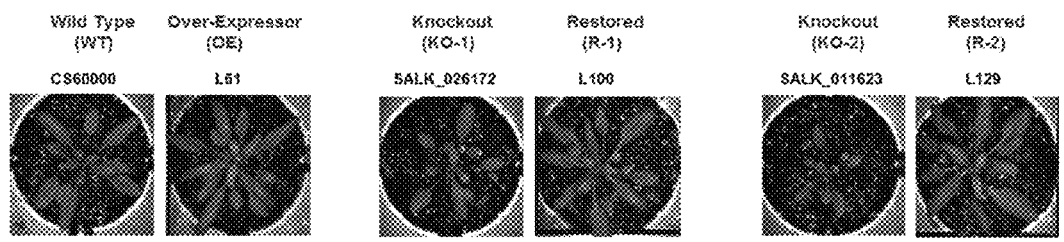
B. Projected leaf area
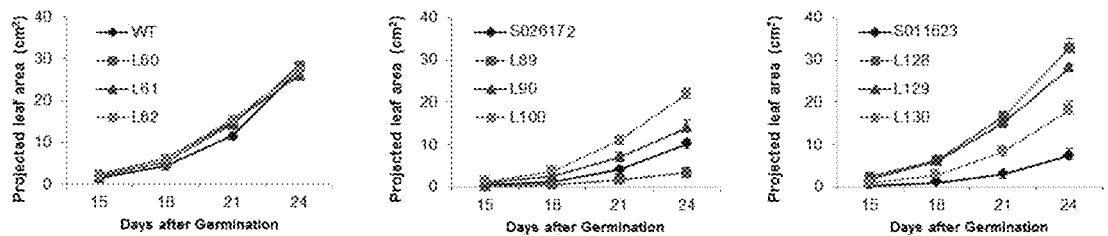
FIG. 19

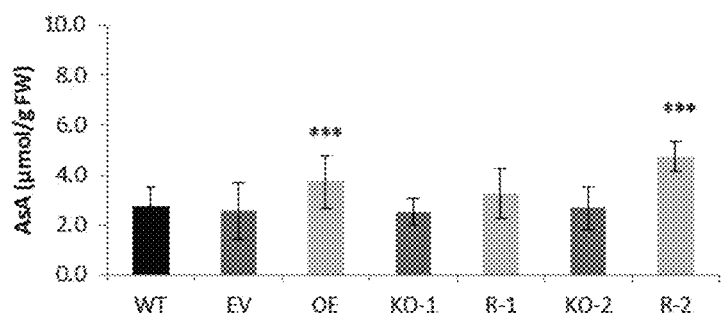
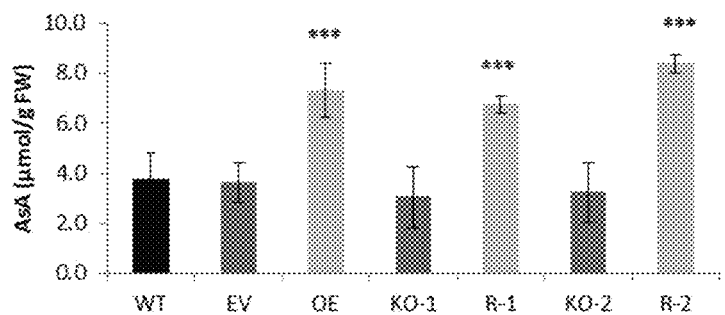
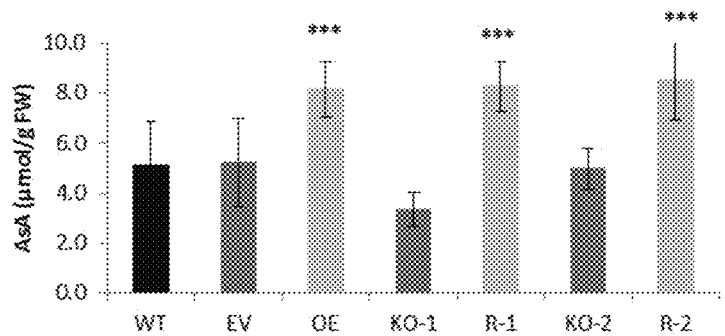
FIG. 21

Dependent Variable: Expression

| Source | DF | Sum of Squares | Mean Square | F Value | Pr > F |
|---|---|---|---|---|---|
| Model | 20 | 810.6441505 | 40.5322075 | 38.61 | <.0001 |
| Error | 160 | 167.9726182 | 1.0498289 | | |
| Corrected Total | 180 | 978.6167688 | | | |

| R-Square | Coeff Var | Root MSE | Expression Mean |
|---|---|---|---|
| 0.782748 | 21.98923 | 1.123266 | 5.108257 |

| Source | DF | Anova SS | Mean Square | F Value | Pr > F |
|---|---|---|---|---|---|
| Light | 2 | 349.1287455 | 174.5643727 | 166.28 | <.0001 |
| Lines | 6 | 418.4714051 | 69.7452342 | 66.43 | <.0001 |
| Light*Lines | 12 | 43.0440000 | 3.5870000 | 3.42 | 0.0002 |

FIG. 22

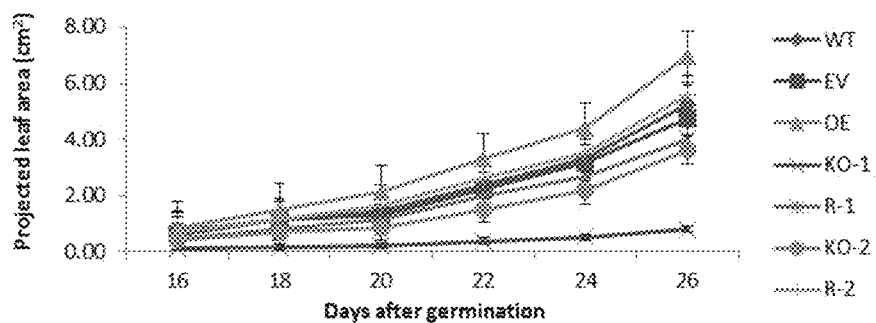
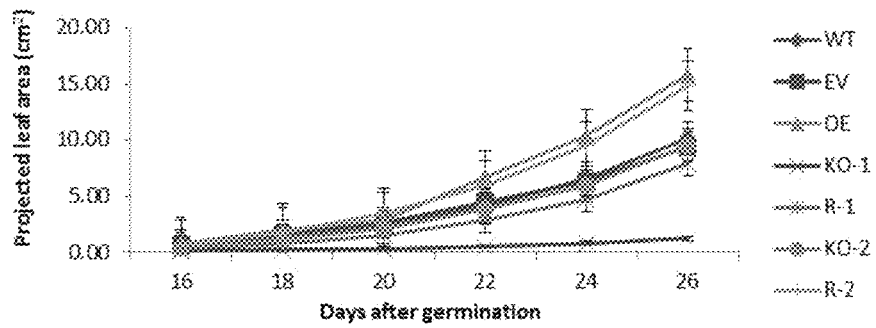
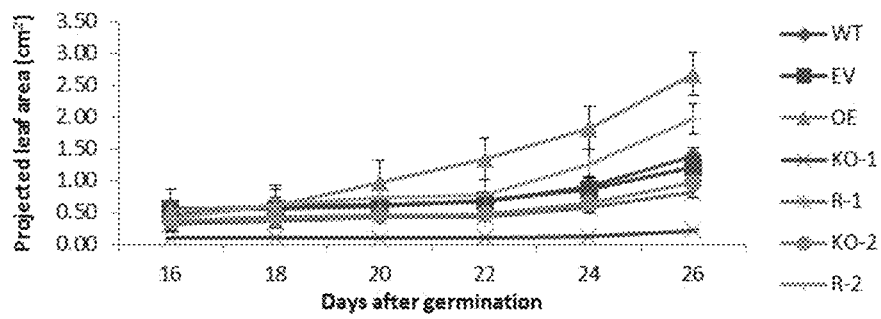
FIG. 23

A. Low light
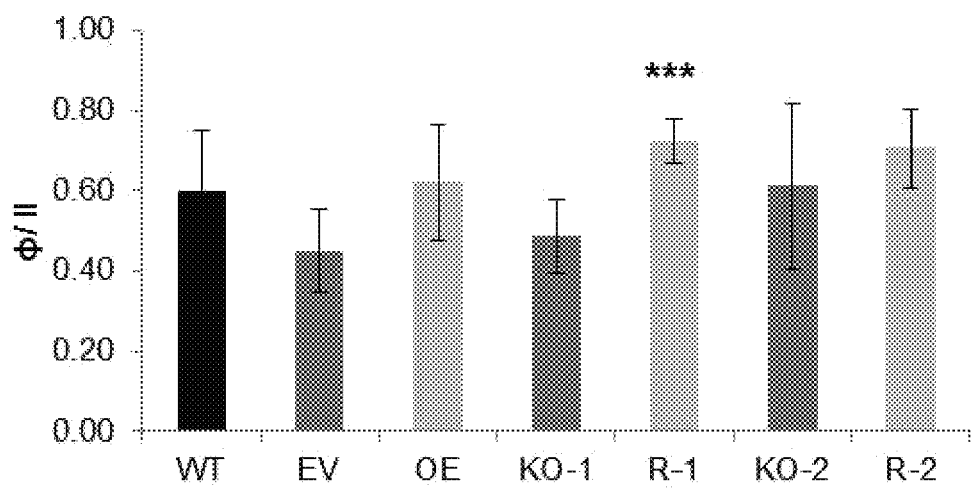
B. Normal light
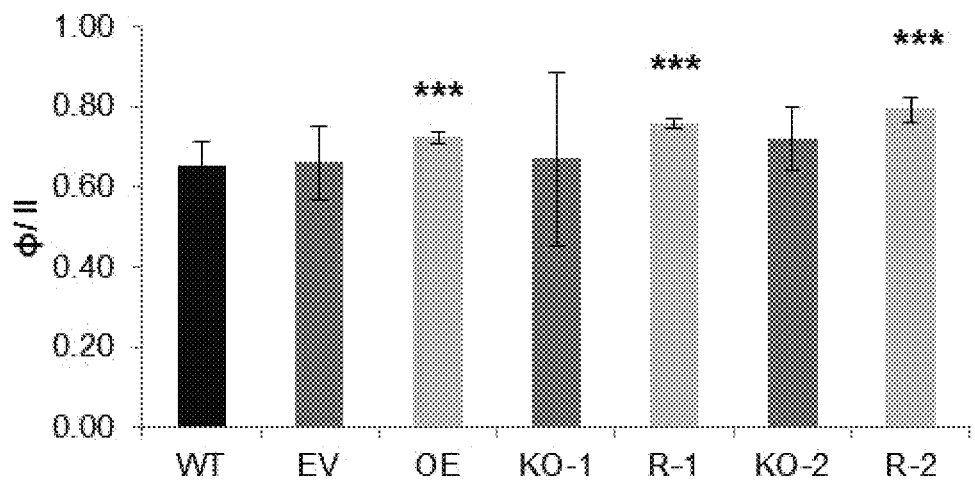
FIG. 26

Dependent Variable: Expression

| Source | DF | Sum of Squares | Mean Square | F Value | Pr > F |
|---|---|---|---|---|---|
| Model | 13 | 1.04174447 | 0.08013419 | 6.59 | <.0001 |
| Error | 112 | 1.36244350 | 0.01216467 | | |
| Corrected Total | 125 | 2.40418797 | | | |

| | R-Square | Coeff Var | Root MSE | Expression Mean |
|---|---|---|---|---|
| | 0.433304 | 0.433304 | 0.110294 | 0.658127 |

| Source | DF | Anova SS | Mean Square | F Value | Pr > F |
|---|---|---|---|---|---|
| Light | 1 | 0.58167212 | 0.09694535 | 7.97 | <.0001 |
| Lines | 6 | 0.34897894 | 0.34897894 | 28.69 | <.0001 |
| Light*Lines | 6 | 0.11109341 | 0.01851557 | 1.52 | 0.1773 |

FIG. 27

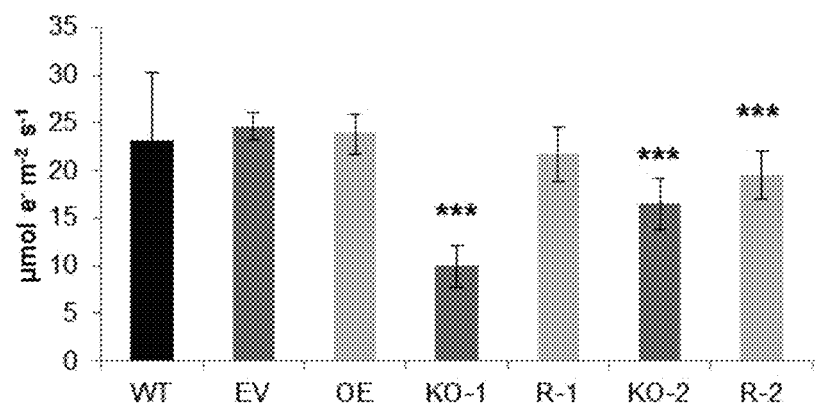
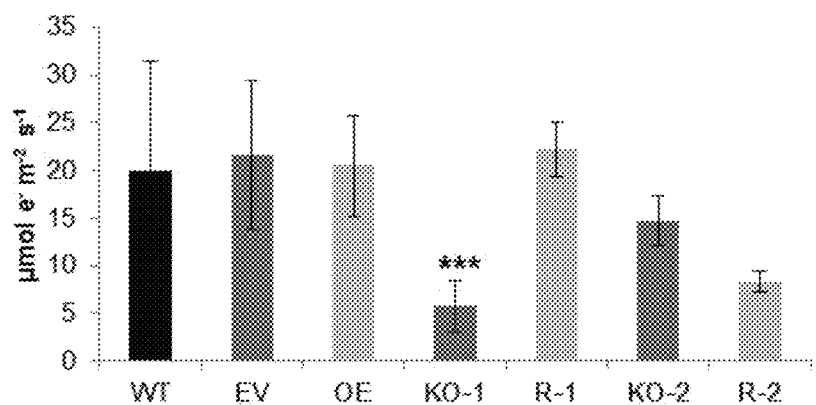
FIG. 28

| Dependent Variable: Expression | | | | | |
|---|---|---|---|---|---|
| Source | DF | Sum of Squares | Mean Square | F Value | Pr > F |
| Model | 13 | 3866.400334 | 297.415410 | 11.17 | <.0001 |
| Error | 112 | 2982.298147 | 26.627662 | | |
| Corrected Total | 125 | 6848.698481 | | | |
| | R-Square | Coeff Var | Root MSE | Expression Mean | |
| | 0.564545 | 27.99361 | 5.160200 | 18.43349 | |
| Source | DF | Anova SS | Mean Square | F Value | Pr > F |
| Light | 1 | 332.376931 | 332.376931 | 12.48 | 0.0006 |
| Lines | 6 | 3052.854000 | 508.809000 | 19.11 | <.0001 |
| Light*Lines | 6 | 481.169403 | 80.194901 | 3.01 | 0.0091 |

FIG. 29

A. Low light
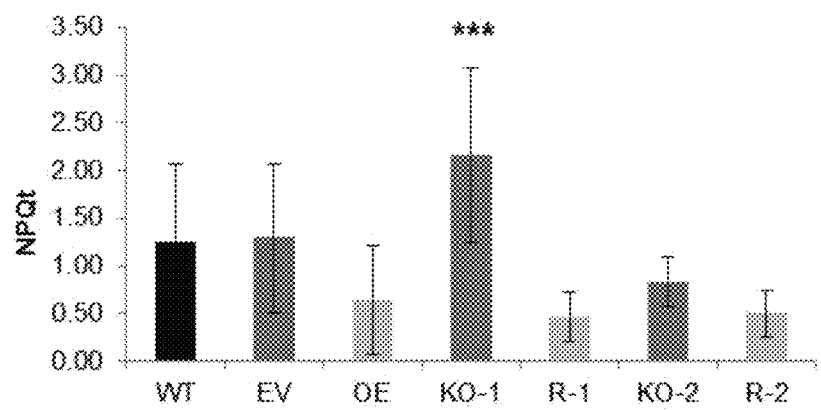
B. Normal light
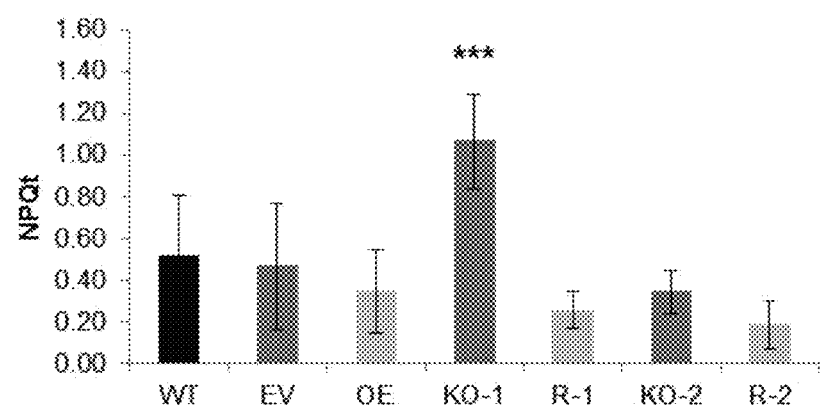
FIG. 30

Dependent Variable: Expression

| Source | DF | Sum of Squares | Mean Square | F Value | Pr > F |
|---|---|---|---|---|---|
| Model | 13 | 28.75697908 | 2.21207531 | 6.19 | <.0001 |
| Error | 112 | 40.02808137 | 0.35739358 | | |
| Corrected Total | 125 | 68.78506044 | | | |

| | R-Square | Coeff Var | Root MSE | Expression Mean |
|---|---|---|---|---|
| | 0.418070 | 86.62722 | 0.597824 | 0.690111 |

| Source | DF | Anova SS | Mean Square | F Value | Pr > F |
|---|---|---|---|---|---|
| Light | 1 | 9.43445128 | 9.43445128 | 26.40 | <.0001 |
| Lines | 6 | 17.23774602 | 2.87295767 | 8.04 | <.0001 |
| Light*Lines | 6 | 2.08478178 | 0.34746363 | 0.97 | 0.4475 |

FIG. 31

| Species | Description |
|---|---|
| 1. Plants | |
| At1g56500 (AtGNL) | |
| Brassica rapa | #Brassica_rapa_:103838684_NHL_repeat-containing_protein_2_(A) |
| Cucumis sativus | #Cucumis_sativus:101222142_NHL_repeat-containing_protein_2_(A) |
| Cucumis melo | #Cucumis_melo:103492110_NHL_repeat-containing_protein_2_(A) |
| Populus trichocarpa | #Populus_trichocarpa_:POPTR_0013s00930g_POPTRDRAFT_1096018_haloacid_dehalogenase-like_hydrolase_family_protein_(A) |
| Jatropha curcas | #Jatropha_curcas:105647432_NHL_repeat-containing_protein_2_(A) |
| Ricinus communis | #Ricinus_communis_:RCOM_1435490_2-deoxyglucose-6-phosphate_phosphatase_putative_(EC:5.4.2.6)_(A) |
| Citrus sinensis | #Citrus_sinensis:102627823_NHL_repeat-containing_protein_2-like_(A) |
| Vitis vinifera | #Vitis_vinifera:100247769_NHL_repeat-containing_protein_2_(A) |
| Theobroma cacao | #Theobroma_cacao:TCM_026778_Haloacid_dehalogenase-like_hydrolase_family_protein_(A) |
| Glycine max | #Glycine_max_:100795843_NHL_repeat-containing_protein_2-like_(A) |
| Prunus mume | #Prunus_mume:103344235_NHL_repeat-containing_protein_2_(A) |
| Fragaria vesca | #Fragaria_vesca:101313042_NHL_repeat-containing_protein_2_(A) |
| Selaginella moellendorffii | #Selaginella_moellendorffii:SELMODRAFT_79954_hypothetical_protein_(A) |
| 2. Animals | |
| Rattus norvegicus | #Rattus_norvegicus:25106_Rgn_GNL_Rc_Reguc_regucalcin_(senescence_marker_protein-30)_(EC:3.1.1.17)_K01053_gluconolactonase_EC:3.1.1.17_(A) |
| Homo sapiens | #Homo_sapiens:9104_RGN_GNL_HEL-S-41_RC_SMP30_regucalcin_(EC:3.1.1.17)_K01053_gluconolactonase_EC:3.1.1.17_(A) |
| Oryctolagus cuniculus 2 | #sp|Q9TTJ6|RGN_RABIT_Regucalcin_OS Oryctolagus_cuniculus_GNRGN_PE2_SV1 |

FIG. 34A

| | |
|---|---|
| *Ovis aries* | #Ovis_aries_(sheep):100171395_RGN_regucalcin_(senescence_marker_protein-30)_(EC:3.1.1.17)_K01053_gluconolactonase_EC:3.1.1.17_(A) |
| *Canis familiaris* | #Canis_familiaris_(dog):480893_RGN_regucalcin_K01053_gluconolactonase_EC:3.1.1.17_(A) |
| *Ailuropoda melanoleuca* | #Ailuropoda_melanoleuca_(giant_panda):100467773_RGN_regucalcin_K01053_gluconolactonase_EC:3.1.1.17_(A) |

3. Bacteria and fungi

| | |
|---|---|
| *Trichoderma reesei* | #Trichoderma_reesei:TRIREDRAFT_62581_gluconolactonase-like_protein_K01053_gluconolactonase_EC:3.1.1.17_(A) |
| *Aspergillus oryzae* | #Aspergillus_oryzae:AOR_1_890114_AO090701000487_protein_AkeP_K01053_gluconolactonase_EC:3.1.1.17_(A) |
| *Zymomonas mobilis* | #sp|Q01578|GNL_ZYMMO_Gluconolactonase_OSZymomonas_mobilis_subsp_mobilis_(strain_ATCC_31821_/_ZM4_/_CP4)_GNgnl_PE1_SV2 |
| *Nostoc punctiforme* | #Nostoc_punctiforme:Npun_F1780_SMP-30/gluconolaconase/LRE_domain-containing_protein_(EC:3.1.1.17)_K01053_gluconolactonase_EC:3.1.1.17_(A) |
| *Pseudomonas syringae* | #Pseudomonas_syringae_pv._tomato_DC3000_gluconolactonase_K01053_gluconolactonase_EC:3.1.1.17_(A) |

4. Bacteria

| | |
|---|---|
| *Pseudomonas monteilii* | #Pseudomonas_monteilii_SB3101:X970_06765_gluconolactonase_K01053_gluconolactonase_EC:3.1.1.17_(A) |

**5. *Arabidopsis thaliana***

AThSS3, AthSS2, AthLAP3, AthSSL2, AThSSL3, AThLAP, AThSCOPL, AThSCOP, AThSSL1, ATSCOP

FIG. 34B

GNL DNA Sequence

```
   1 ATGGCTTTGA AACTCACTTC TCCGCCTTCA GTTTTCTCAC AATCAAGGAG
  51 ATTATCTTCT TCTTCGTTAA TTCCGATAAG GTCAAAATCC ACATTCACCG
 101 GATTTCGATC GAGAACCGGT GTTTATTTAA GCAAAACGAC GGCGCTTCAG
 151 TCGTCTACAA AACTGAGTGT GGCAGCGGAG AGTCCTGCGG CGACAATTGC
 201 GACGGATGAT TGGGGGAAAG TGTCGGCGGT TCTGTTTGAT ATGGACGGTG
 251 TGCTTTGTAA CAGTGAAGAT CTTTCTAGAC GCGCCGCCGT GGATGTTTTT
 301 ACGGAGATGG GAGTTGAAGT CACTGTGGAC GATTTCGTTC CTTTTATGGG
 351 AACAGGTGAA GCCAAGTTTT TAGGAGGTGT TGCTTCAGTC AAAGAAGTTA
 401 AAGGATTTGA TCCAGATGCA GCTAAAGAGA GATTCTTTGA AATATATCTC
 451 GATAAGTATG CGAAGCCAGA ATCTGGGATT GGATTTCCAG GAGCATTGGA
 501 GCTTGTTACT GAGTGTAAGA ACAAAGGCCT TAAAGTCGCT GTTGCATCTA
 551 GTGCTGACCG TATCAAAGTT GATGCGAATC TGAAAGCTGC TGGTTTGTCT
 601 TTGACCATGT TTGATGCCAT TGTTTCAGCA GACGCCTTTG AGAATTTGAA
 651 ACCAGCTCCA GATATTTTCC TGGCTGCTGC AAAGATCTTA GGTGTGCCTA
 701 CCAGCGAGTG TGTTGTTATT GAAGATGCGC TTGCTGGAGT CCAAGCCGCA
 751 CAAGCTGCGA ACATGAGATG TATAGCCGTA AAAACTACTT TATCTGAAGC
 801 AATTCTTAAG GATGCTGGTC CTTCTATGAT ACGAGACGAT ATTGGAAACA
 851 TCTCAATCAA TGACATTCTC ACTGGTGGCT CAGATTCTAC CAGAAATTCC
 901 ACAGCAATGC TTGAAGAGAA CACGGTCAGC GACAAAACCA GCGCTAACGG
 951 GTTTCAGGGC TCTCGACGAG ATATACTGAG GTATGGGAGT CTTGGCATTG
1001 CTCTTTCTTG TGTCTACTTC GCCGCCACCA ACTGGAAGGC AATGCAATAT
1051 GCTTCTCCGA AAGCTTTGTG GAATGCATTG GTTGGAGCAA AAAGCCCTTC
1101 TTTTACACAG AACCAAGGTG AAGGGAGAGT GCAACAGTTC GTCGATTACA
1151 TTGCTGATCT AGAGAGCAAG CAAACAGCTA AACTGTGCC AGAATTCCCA
1201 TCTAAACTCG ACTGGCTAAA CACTGCCCCT CTCCAGTTTC GCCGGGATTT
1251 AAAAGGGAAA GTGGTTATAC TTGATTTTTG GACCTATTGC TGCATAAACT
1301 GTATGCATGT ATTACCGGAT CTAGAGTTTC TTGAGAAGAA GTACAAGGAT
```

FIG. 36A

```
1351 ATGCCATTCA CCGTTGTGGG TGTACACTCG GCTAAGTTCG ACAATGAGAA
1401 AGATTTAGAT GCCATACGAA ATGCAGTTCT TCGCTATGAT ATTAGCCACC
1451 CGGTTGTGAA TGATGGAGAC ATGTACATGT GGAGAGAGCT TGGCATCAAC
1501 TCGTGGCCTA CATTTGCTGT TGTTTCTCCT AATGGCAAAG TCATTGCACA
1551 AATTGCCGGA GAAGGTCACC GCAAAGATCT TGATGACGTG GTGGCGGCAG
1601 CTCTGACATA TTATGGTGGA AAGAATGTAT TAGACAGTAC TCCGCTTCCA
1651 ACACGTTTGG AGAAAGACAA CGATCCACGT TTGGCCACGT CTCCGTTGAA
1701 ATTTCCGGGA AAGTTGGCTA TTGATACTCT TAATAACAGG CTATTCATCT
1751 CAGACAGTAA CCATAACCGT ATTATTGTAA CTGATCTCGA AGGAAATTTC
1801 ATAGTCCAAA TTGGCAGCAG TGGAGAAGAA GGTTTCCAAG ATGGTTCCTT
1851 CGAAGATGCT GCATTTAATC GTCCTCAGGG ACTAGCTTAT AATGCTAAGA
1901 AGAATCTTCT TTATGTTGCT GACACCGAGA ATCATGCTTT GAGAGAGATT
1951 GATTTTGTCA ACGAGAGAGT ACAGACTCTG GCTGGTAATG GAACTAAAGG
2001 CTCAGACTAC CAAGGTGGAA GAAAAGGAAC CAAACAGCTT TTGAATTCTC
2051 CTTGGGACGT ATGCTTTGAG CCGGTGAATG AGAAGGTATA CATTGCAATG
2101 GCAGGTCAGC ACCAGATTTG GGAATACAGT GTGCTTGATG GTATTACTCG
2151 AGTTTTCAGT GGAAATGGTT ATGAAAGAAA CCTCAACGGT TCCACCCCTC
2201 AGACTACATC ATTTGCTCAG CCATCAGGAA TCTCATTAGG CCCTGATTTG
2251 AAAGAAGCAT ATATTGCTGA TAGCGAGAGC AGTTCTATTC GTGCCCTTGA
2301 TCTTCAAACT GGAGGATCAA GATTACTTGC GGGTGGTGAT CCGTATTTCT
2351 CTGAGAATCT TTTCAAGTTT GGAGACAATG ATGGCGTGGG AGCAGAAGTT
2401 CTCCTACAAC ACCCGCTAGG TGTATTATGC GCAAATGATG GTCAAATATA
2451 TCTAACTGAT AGCTATAACC ACAAGATTAA GAAGTTGGAC CCTGTAACCA
2501 AACGTGTTGT TACTCTCGCT GGAACGGGAA AAGCCGGTTT TAAGGATGGG
2551 AAGGTCAAGG GTGCTCAGCT TTCAGAGCCT GCAGGACTTG CTATAACTGA
2601 AAACGGGAGG CTGTTTGTGG CGGATACAAA TAATAGCCTT ATCCGATACA
2651 TAGATTTGAA CAAAGGAGAA GACTCAGAGA TTCTTACATT GGAGTTAAAA
2701 GGTGTTCAAC CACCAACGCC AAAGGCAAAA TCCCTGAAAC GTTTGAGAAA
2751 ACGTGCCTCG GCTGATACAA AGATTGTCAA AGTGGATTCT GTAACGTCCC
2801 GTGAAGGAGA TTTGAATCTC AAAATCTCAT TACCAGATGG CTACCATTTC
2851 TCCAAGGAAG CGCGGAGTAA GTTTGTGGTT GATGTGGAGC CTGAAAACGC
```

FIG. 36B

```
2901 AGTAGCAATC GATCCAACGG AAGGAACTCT GAGTCCCGAA GGTTCAACAA

2951 TGCTTCATTT TATACAATCT TCAACTTCGG CTTCTGTTGG GAAAATCAGT

3001 TGCAAGGTGT ACTATTGCAA AGAAGACGAG GTTTGCTTGT ATCAGTCTGT

3051 ACAGTTTGAG GTCCCTTTCA AGGTGGAATC AGAATTATCT GCTTCTCCGA

3101 CAATCACATT CACGGTTACA CCGAGAGCAC CCGATGCTGG TGGGTTACAG

3151 CTTCAAGGTA CTCGCTGA
```

FIG. 36C

GNL Amino Acid Sequence

```
   1  MALKLTSPPS  VFSQSRRLSS  SSLIPIRSKS  TFTGFRSRTG  VYLSKTTALQ
  51  SSTKLSVAAE  SPAATIATDD  WGKVSAVLFD  MDGVLCNSED  LSRRAAVDVF
 101  TEMGVEVTVD  DFVPFMGTGE  AKFLGGVASV  KEVKGFDPDA  AKERFFEIYL
 151  DKYAKPESGI  GFPGALELVT  ECKNKGLKVA  VASSADRIKV  DANLKAAGLS
 201  LTMFDAIVSA  DAFENLKPAP  DIFLAAAKIL  GVPTSECVVI  EDALAGVQAA
 251  QAANMRCIAV  KTTLSEAILK  DAGPSMIRDD  IGNISINDIL  TGGSDSTRNS
 301  TAMLEENTVS  DKTSANGFQG  SRRDILRYGS  LGIALSCVYF  AATNWKAMQY
 351  ASPKALWNAL  VGAKSPSFTQ  NQGEGRVQQF  VDYIADLESK  QTATTVPEFP
 401  SKLDWLNTAP  LQFRRDLKGK  VVILDFWTYC  CINCMHVLPD  LEFLEKKYKD
 451  MPFTVVGVHS  AKFDNEKDLD  AIRNAVLRYD  ISHPVVNDGD  MYMWRELGIN
 501  SWPTFAVVSP  NGKVIAQIAG  EGHRKDLDDV  VAAALTYYGG  KNVLDSTPLP
 551  TRLEKDNDPR  LATSPLKFPG  KLAIDTLNNR  LFISDSNHNR  IIVTDLEGNF
 601  IVQIGSSGEE  GFQDGSFEDA  AFNRPQGLAY  NAKKNLLYVA  DTENHALREI
 651  DFVNERVQTL  AGNGTKGSDY  QGGRKGTKQL  LNSPWDVCFE  PVNEKVYIAM
 701  AGQHQIWEYS  VLDGITRVFS  GNGYERNLNG  STPQTTSFAQ  PSGISLGPDL
 751  KEAYIADSES  SSIRALDLQT  GGSRLLAGGD  PYFSENLFKF  GDNDGVGAEV
 801  LLQHPLGVLC  ANDGQIYLTD  SYNHKIKKLD  PVTKRVVTLA  GTGKAGFKDG
 851  KVKGAQLSEP  AGLAITENGR  LFVADTNNSL  IRYIDLNKGE  DSEILTLELK
 901  GVQPPTPKAK  SLKRLRKRAS  ADTKIVKVDS  VTSREGDLNL  KISLPDGYHF
 951  SKEARSKFVV  DVEPENAVAI  DPTEGTLSPE  GSTMLHFIQS  STSASVGKIS
1001  CKVYYCKEDE  VCLYQSVQFE  VPFKVESELS  ASPTITFTVT  PRAPDAGGLQ
1051  LQGTR
```

FIG. 37

SEQUENCE LISTING

<160> NUMBER OF SEQ ID NOS: 2

<210> SEQ ID NO 1

<211> LENGTH: 3168
<212> TYPE: DNA
<213> ORGANISM: Arabidopsis thaliana

<400> SEQUENCE: 1

| | | | | | |
|---|---|---|---|---|---|
| atggctttga | aactcacttc | tccgccttca | gttttctcac | aatcaaggag | attatcttct | 60 |
| tcttcgttaa | ttccgataag | gtcaaaatcc | acattcaccg | gatttcgatc | gagaaccggt | 120 |
| gtttatttaa | gcaaaacgac | ggcgcttcag | tcgtctacaa | aactgagtgt | ggcagcggag | 180 |
| agtcctgcgg | cgacaattgc | gacggatgat | tgggggaaag | tgtcggcggt | tctgtttgat | 240 |
| atggacggtg | tgctttgtaa | cagtgaagat | cttctagac | gcgccgccgt | ggatgttttt | 300 |
| acggagatgg | gagttgaagt | cactgtggac | gatttcgttc | cttttatggg | aacaggtgaa | 360 |
| gccaagtttt | taggaggtgt | tgcttcagtc | aaagaagtta | aaggatttga | tccagatgca | 420 |
| gctaaagaga | gattctttga | aatatatctc | gataagtatg | cgaagccaga | atctgggatt | 480 |
| ggatttccag | gagcattgga | gcttgttact | gagtgtaaga | caaaggcct | taaagtcgct | 540 |
| gttgcatcta | gtgctgaccg | tatcaaagtt | gatgcgaatc | tgaaagctgc | tggtttgtct | 600 |
| ttgaccatgt | ttgatgccat | tgtttcagca | gacgcctttg | agaatttgaa | accagctcca | 660 |
| gatattttcc | tggctgctgc | aaagatctta | ggtgtgccta | ccagcgagtg | tgttgttatt | 720 |
| gaagatgcgc | ttgctggagt | ccaagccgca | caagctgcga | acatgagatg | tatagccgta | 780 |
| aaaactactt | tatctgaagc | aattcttaag | gatgctggtc | cttctatgat | acgagacgat | 840 |
| attggaaaca | tctcaatcaa | tgacattctc | actggtggct | cagattctac | cagaaattcc | 900 |
| acagcaatgc | ttgaagagaa | cacggtcagc | gacaaaacca | cgctaacgg | gtttcagggc | 960 |
| tctcgacgag | atatactgag | gtatgggagt | cttggcattg | ctctttcttg | tgtctacttc | 1020 |
| gccgccacca | actggaaggc | aatgcaatat | gcttctccga | agctttgtg | gaatgcattg | 1080 |
| gttggagcaa | aaagcccttc | ttttacacag | aaccaaggtg | aagggagagt | gcaacagttc | 1140 |
| gtcgattaca | ttgctgatct | agagagcaag | caaacagcta | caactgtgcc | agaattccca | 1200 |
| tctaaactcg | actggctaaa | cactgccccct | ctccagtttc | gccgggattt | aaaagggaaa | 1260 |
| gtggttatac | ttgattttg | gacctattgc | tgcataaact | gtatgcatgt | attaccggat | 1320 |
| ctagagtttc | ttgagaagaa | gtacaaggat | atgccattca | ccgttgtggg | tgtacactcg | 1380 |
| gctaagttcg | acaatgagaa | agatttagat | gccatacgaa | atgcagttct | tcgctatgat | 1440 |
| attagccacc | cggttgtgaa | tgatggagac | atgtacatgt | ggagagagct | tggcatcaac | 1500 |
| tcgtggccta | catttgctgt | tgtttctcct | aatggcaaag | tcattgcaca | aattgccgga | 1560 |
| gaaggtcacc | gcaaagatct | tgatgacgtg | gtggcggcag | ctctgacata | ttatggtgga | 1620 |
| aagaatgtat | tagacagtac | tccgcttcca | acacgtttgg | agaaagacaa | cgatccacgt | 1680 |
| ttggccacgt | ctccgttgaa | atttccggga | aagttggcta | ttgatactct | taataacagg | 1740 |
| ctattcatct | cagacagtaa | ccataaccgt | attattgtaa | ctgatctcga | aggaaatttc | 1800 |
| atagtccaaa | ttggcagcag | tggagaagaa | ggtttccaag | atggttcctt | cgaagatgct | 1860 |
| gcatttaatc | gtcctcaggg | actagcttat | aatgctaaga | agaatcttct | ttatgttgct | 1920 |
| gacaccgaga | atcatgcttt | gagagagatt | gattttgtca | acgagagagt | acagactctg | 1980 |
| gctggtaatg | gaactaaagg | ctcagactac | caaggtggaa | gaaaaggaac | caaacagctt | 2040 |
| ttgaattctc | cttgggacgt | atgctttgag | ccggtgaatg | agaaggtata | cattgcaatg | 2100 |
| gcaggtcagc | accagatttg | gaatacagt | gtgcttgatg | gtattactcg | agttttcagt | 2160 |
| ggaaatggtt | atgaaagaaa | cctcaacggt | tccaccccctc | agactacatc | atttgctcag | 2220 |

-continued

```
ccatcaggaa tctcattagg ccctgatttg aaagaagcat atattgctga tagcgagagc    2280
agttctattc gtgcccttga tcttcaaact ggaggatcaa gattacttgc gggtggtgat    2340
ccgtatttct ctgagaatct tttcaagttt ggagacaatg atggcgtggg agcagaagtt    2400
ctcctacaac acccgctagg tgtattatgc gcaaatgatg gtcaaatata tctaactgat    2460
agctataacc acaagattaa gaagttggac cctgtaacca acgtgttgt tactctcgct     2520
ggaacgggaa aagccggttt taaggatggg aaggtcaagg gtgctcagct ttcagagcct    2580
gcaggacttg ctataactga aaacgggagg ctgtttgtgg cggatacaaa taatagcctt    2640
atccgataca tagatttgaa caaaggagaa gactcagaga ttcttacatt ggagttaaaa    2700
ggtgttcaac caccaacgcc aaaggcaaaa tccctgaaac gtttgagaaa acgtgcctcg    2760
gctgatacaa agattgtcaa agtggattct gtaacgtccc gtgaaggaga tttgaatctc    2820
aaaatctcat taccagatgg ctaccatttc tccaaggaag cgcggagtaa gtttgtggtt    2880
gatgtggagc ctgaaaacgc agtagcaatc gatccaacgg aaggaactct gagtcccgaa    2940
ggttcaacaa tgcttcattt tatacaatct tcaacttcgg cttctgttgg gaaaatcagt    3000
tgcaaggtgt actattgcaa agaagacgag gtttgcttgt atcagtctgt acagtttgag    3060
gtccctttca aggtggaatc agaattatct gcttctccga caatcacatt cacggttaca    3120
ccgagagcac ccgatgctgg tgggttacag cttcaaggta ctcgctga                3168
```

```
<210> SEQ ID NO 2
<211> LENGTH: 1055
<212> TYPE: PRT
<213> ORGANISM: Arabidopsis thaliana

<400> SEQUENCE: 2
```

Met Ala Leu Lys Leu Thr Ser Pro Pro Ser Val Phe Ser Gln Ser Arg
1               5                   10                  15

Arg Leu Ser Ser Ser Leu Ile Pro Ile Arg Ser Lys Ser Thr Phe
            20                  25                  30

Thr Gly Phe Arg Ser Arg Thr Gly Val Tyr Leu Ser Lys Thr Thr Ala
        35                  40                  45

Leu Gln Ser Ser Thr Lys Leu Ser Val Ala Ala Glu Ser Pro Ala Ala
    50                  55                  60

Thr Ile Ala Thr Asp Asp Trp Gly Lys Val Ser Ala Val Leu Phe Asp
65                  70                  75                  80

Met Asp Gly Val Leu Cys Asn Ser Glu Asp Leu Ser Arg Arg Ala Ala
                85                  90                  95

Val Asp Val Phe Thr Glu Met Gly Val Glu Val Thr Val Asp Asp Phe
            100                 105                 110

Val Pro Phe Met Gly Thr Gly Glu Ala Lys Phe Leu Gly Gly Val Ala
        115                 120                 125

Ser Val Lys Glu Val Lys Gly Phe Asp Pro Asp Ala Ala Lys Glu Arg
    130                 135                 140

Phe Phe Glu Ile Tyr Leu Asp Lys Tyr Ala Lys Pro Glu Ser Gly Ile
145                 150                 155                 160

Gly Phe Pro Gly Ala Leu Glu Leu Val Thr Glu Cys Lys Asn Lys Gly
                165                 170                 175

Leu Lys Val Ala Val Ala Ser Ser Ala Asp Arg Ile Lys Val Asp Ala
            180                 185                 190

Asn Leu Lys Ala Ala Gly Leu Ser Leu Thr Met Phe Asp Ala Ile Val
        195                 200                 205

```
Ser Ala Asp Ala Phe Glu Asn Leu Lys Pro Ala Pro Asp Ile Phe Leu
    210                 215                 220

Ala Ala Ala Lys Ile Leu Gly Val Pro Thr Ser Glu Cys Val Val Ile
225                 230                 235                 240

Glu Asp Ala Leu Ala Gly Val Gln Ala Gln Ala Ala Asn Met Arg
                    245                 250                 255

Cys Ile Ala Val Lys Thr Thr Leu Ser Glu Ala Ile Leu Lys Asp Ala
                260                 265                 270

Gly Pro Ser Met Ile Arg Asp Asp Ile Gly Asn Ile Ser Ile Asn Asp
            275                 280                 285

Ile Leu Thr Gly Gly Ser Asp Ser Thr Arg Asn Ser Thr Ala Met Leu
    290                 295                 300

Glu Glu Asn Thr Val Ser Asp Lys Thr Ser Ala Asn Gly Phe Gln Gly
305                 310                 315                 320

Ser Arg Arg Asp Ile Leu Arg Tyr Gly Ser Leu Gly Ile Ala Leu Ser
                325                 330                 335

Cys Val Tyr Phe Ala Ala Thr Asn Trp Lys Ala Met Gln Tyr Ala Ser
                340                 345                 350

Pro Lys Ala Leu Trp Asn Ala Leu Val Gly Ala Lys Ser Pro Ser Phe
            355                 360                 365

Thr Gln Asn Gln Gly Glu Gly Arg Val Gln Gln Phe Val Asp Tyr Ile
    370                 375                 380

Ala Asp Leu Glu Ser Lys Gln Thr Ala Thr Thr Val Pro Glu Phe Pro
385                 390                 395                 400

Ser Lys Leu Asp Trp Leu Asn Thr Ala Pro Leu Gln Phe Arg Arg Asp
                405                 410                 415

Leu Lys Gly Lys Val Val Ile Leu Asp Phe Trp Thr Tyr Cys Cys Ile
                420                 425                 430

Asn Cys Met His Val Leu Pro Asp Leu Glu Phe Leu Glu Lys Lys Tyr
            435                 440                 445

Lys Asp Met Pro Phe Thr Val Val Gly Val His Ser Ala Lys Phe Asp
    450                 455                 460

Asn Glu Lys Asp Leu Asp Ala Ile Arg Asn Ala Val Leu Arg Tyr Asp
465                 470                 475                 480

Ile Ser His Pro Val Val Asn Asp Gly Asp Met Tyr Met Trp Arg Glu
                485                 490                 495

Leu Gly Ile Asn Ser Trp Pro Thr Phe Ala Val Val Ser Pro Asn Gly
            500                 505                 510

Lys Val Ile Ala Gln Ile Ala Gly Glu Gly His Arg Lys Asp Leu Asp
    515                 520                 525

Asp Val Val Ala Ala Leu Thr Tyr Tyr Gly Gly Lys Asn Val Leu
530                 535                 540

Asp Ser Thr Pro Leu Pro Thr Arg Leu Glu Lys Asp Asn Asp Pro Arg
545                 550                 555                 560

Leu Ala Thr Ser Pro Leu Lys Phe Pro Gly Lys Leu Ala Ile Asp Thr
                565                 570                 575

Leu Asn Asn Arg Leu Phe Ile Ser Asp Ser Asn His Asn Arg Ile Ile
            580                 585                 590

Val Thr Asp Leu Glu Gly Asn Phe Ile Val Gln Ile Gly Ser Ser Gly
    595                 600                 605

Glu Glu Gly Phe Gln Asp Gly Ser Phe Glu Asp Ala Ala Phe Asn Arg
610                 615                 620
```

```
Pro Gln Gly Leu Ala Tyr Asn Ala Lys Lys Asn Leu Leu Tyr Val Ala
625                 630                 635                 640

Asp Thr Glu Asn His Ala Leu Arg Glu Ile Asp Phe Val Asn Glu Arg
            645                 650                 655

Val Gln Thr Leu Ala Gly Asn Gly Thr Lys Gly Ser Asp Tyr Gln Gly
            660                 665                 670

Gly Arg Lys Gly Thr Lys Gln Leu Leu Asn Ser Pro Trp Asp Val Cys
        675                 680                 685

Phe Glu Pro Val Asn Glu Lys Val Tyr Ile Ala Met Ala Gly Gln His
        690                 695                 700

Gln Ile Trp Glu Tyr Ser Val Leu Asp Gly Ile Thr Arg Val Phe Ser
705                 710                 715                 720

Gly Asn Gly Tyr Glu Arg Asn Leu Asn Gly Ser Thr Pro Gln Thr Thr
            725                 730                 735

Ser Phe Ala Gln Pro Ser Gly Ile Ser Leu Gly Pro Asp Leu Lys Glu
            740                 745                 750

Ala Tyr Ile Ala Asp Ser Glu Ser Ser Ile Arg Ala Leu Asp Leu
        755                 760                 765

Gln Thr Gly Gly Ser Arg Leu Leu Ala Gly Gly Asp Pro Tyr Phe Ser
770                 775                 780

Glu Asn Leu Phe Lys Phe Gly Asp Asn Asp Gly Val Gly Ala Glu Val
785                 790                 795                 800

Leu Leu Gln His Pro Leu Gly Val Leu Cys Ala Asn Asp Gly Gln Ile
            805                 810                 815

Tyr Leu Thr Asp Ser Tyr Asn His Lys Ile Lys Lys Leu Asp Pro Val
            820                 825                 830

Thr Lys Arg Val Val Thr Leu Ala Gly Thr Gly Lys Ala Gly Phe Lys
        835                 840                 845

Asp Gly Lys Val Lys Gly Ala Gln Leu Ser Glu Pro Ala Gly Leu Ala
        850                 855                 860

Ile Thr Glu Asn Gly Arg Leu Phe Val Ala Asp Thr Asn Asn Ser Leu
865                 870                 875                 880

Ile Arg Tyr Ile Asp Leu Asn Lys Gly Glu Asp Ser Glu Ile Leu Thr
            885                 890                 895

Leu Glu Leu Lys Gly Val Gln Pro Pro Thr Pro Lys Ala Lys Ser Leu
            900                 905                 910

Lys Arg Leu Arg Lys Arg Ala Ser Ala Asp Thr Lys Ile Val Lys Val
        915                 920                 925

Asp Ser Val Thr Ser Arg Glu Gly Asp Leu Asn Leu Lys Ile Ser Leu
        930                 935                 940

Pro Asp Gly Tyr His Phe Ser Lys Glu Ala Arg Ser Lys Phe Val Val
945                 950                 955                 960

Asp Val Glu Pro Glu Asn Ala Val Ala Ile Asp Pro Thr Glu Gly Thr
            965                 970                 975

Leu Ser Pro Glu Gly Ser Thr Met Leu His Phe Ile Gln Ser Ser Thr
            980                 985                 990

Ser Ala Ser Val Gly Lys Ile Ser Cys Lys Val Tyr Tyr Cys Lys Glu
        995                 1000                1005

Asp Glu Val Cys Leu Tyr Gln Ser Val Gln Phe Glu Val Pro Phe
        1010                1015                1020
```

-continued

```
Lys Val Glu Ser Glu Leu Ser Ala Ser Pro Thr Ile Thr Phe Thr
    1025                1030            1035

Val Thr Pro Arg Ala Pro Asp Ala Gly Gly Leu Gln Leu Gln Gly
    1040                1045            1050

Thr Arg
    1055
```

METHOD OF IMPROVING CHLOROPLAST FUNCTION AND INCREASING SEED YIELD

CROSS-REFERENCE TO RELATED APPLICATIONS

This application claims priority to and is a continuation in part of U.S. Patent Application No. 62/428,775 entitled "Method of Improving Chloroplast Function" filed on Dec. 1, 2016.

REFERENCE TO SEQUENCE LISTING SUBMITTED VIA EFS-WEB

The official copy of the sequence listing is submitted electronically via EFS-WEB as an ASCII (.txt) formatted sequence listing with a file named 2018-01-11-US_ST25.txt, created on Jan. 11, 2018 and having a size of 14 KB and accompanies this specification. The sequence listing contained in this ASCII formatted document is part of the specification and is herein incorporated by reference in its entirety and includes no new matter.

STATEMENT REGARDING FEDERALLY SPONSORED RESEARCH OR DEVELOPMENT

Not Applicable.

REFERENCE TO A MICROFICHE APPENDIX

Not Applicable.

RESERVATION OF RIGHTS

A portion of the disclosure of this patent document contains material which is subject to intellectual property rights such as but not limited to copyright, trademark, and/or trade dress protection. The owner has no objection to the facsimile reproduction by anyone of the patent document or the patent disclosure as it appears in the Patent and Trademark Office patent files or records but otherwise reserves all rights whatsoever.

BACKGROUND OF THE INVENTION

1. Field of the Invention 1.1. Vitamin C

Vitamin C (a.k.a. L-ascorbic acid, AsA) is the most abundant water-soluble antioxidant found in plants (Smirnoff, 2000). In the late 1750's it was established that citrus fruits contained a "cure" for scurvy a.k.a. "sea plague". However it was 1928 when Albert Szent-Györi isolated ascorbate and identified it as the anti-scorbutic component present in citrus and other fruits. Since then, a significant body of evidence has been accumulated about the importance of vitamin C for human and animal health (Drouin et al., 2011; Padayatty, 2016).

Ascorbate is a non-enzymatic antioxidant with a simple molecular structure. As is true for many other antioxidants, vitamin C is present in plants in two forms, the reduced and most active form called ascorbate and the oxidized form named dehydroascorbate. The chemical structure of ascorbate (AsA) and dehydroascorbate (DHA), the reduced and oxidized forms of vitamin C, are shown in FIG. 1. Ascorbate belongs to the family of six carbon sugars with a conjugated pi enediol system at carbons 2 and 3. Ascorbate is a very effective antioxidant due to its ability to donate a pair of electrons and stabilize the subsequent charge using the two oxygen atoms at C2 and C3 in the oxidized form of the molecule (Lee et al., 2006). Ascorbate eliminates reactive oxygen species (ROS) from both inside and outside cells, because it is able to pass through the cell membrane in its oxidized form where it reduces the lipophilic α-tocopherol (vitamin E) which is membrane bound in its oxidized state. This makes ascorbate an important part of the enzymatic antioxidant cycle in recycling other important antioxidants which would otherwise be lost to the cell (Traber and Stevens, 2011).

1.2. Importance of Ascorbate in Humans

Humans, primates, and a few other animals including teleost fishes, guinea pigs, some bats and passeriforme birds cannot synthesize vitamin C due to of the lack of an active L-gulono-1,4-lactone oxidase (GuILO) (Drouin et al., 2011). This enzyme catalyzes the last step in vitamin C biosynthesis, and it is highly mutated and non-functional in these species (Sato et al., 1976). Humans and other animals need to consume this essential vitamin from fresh fruits and vegetables to satisfy their needs.

In animals, vitamin C is involved in the synthesis of collagen, an important component of the skin, scar tissue, tendons, ligaments, and blood vessels (Levine et al., 1995; Davey et al., 2000). Another essential role of vitamin C is related to its function in redox homeostasis; this means when the production of ROS increases, the body's response will increase the activity of the endogenous antioxidant system through redox signaling (Figueroa-Méndez and Rivas Arancibia, 2015). Vitamin C functions in oxidative protein folding and in the maintenance of the intraluminal oxidative environment, which suggests that it has a particular role in endoplasmic reticulum related processes (Mandl et al., 2009). In animals, vitamin C interacts enzymatically and non-enzymatically with ROS. In humans vitamin C is essential in preventing pathological conditions including cardiovascular disease, cancer, hepatitis, bacterial infections, fungal infection, and allergies (Cathcart, 1981; Padayatty et al., 2006). The two-time Nobel Prize-winner, Linus Pauling, demonstrated that cancer patients treated with high doses of vitamin C had an increased survival rate (Cameron and Pauling, 1976). Recently Yun et al., (2015) showed that high levels of vitamin C killed human colorectal cancer cells. This effect is due to increased uptake of dehydroascorbate, the oxidized form of the molecule. Vitamin C has a uricosuric effect in humans and decreases uric acid levels, exerting a protective effect on gout (Stamp et al., 2013).

1.3. Importance of Ascorbate in Plants

In plants, ascorbate (AsA) has a wide variety of physiological roles. It functions as an enzyme cofactor, as a radical scavenger, and as donor/acceptor of electron transport in the chloroplast (Conklin and Barth, 2004; Ishikawa et al., 2006). Ascorbate can protect tissues against damage caused by ROS produced through normal oxygenic metabolism or generated from biotic and abiotic stress, and is strongly associated with photosynthesis and respiration. Reactive oxygen species include molecules such as superoxide and hydrogen peroxide.

Chloroplasts as well as mitochondria produce ROS as byproducts of normal cellular metabolism, but this production is enhanced by a variety of environmental stresses (Conklin et al., 1996; Conklin and Barth, 2004). Another essential role of AsA is the modulation of processes such as lignification, cell division, cell elongation, the hypersensitive response, tolerance to stresses, and senescence in plants (Smirnoff and Wheeler, 2000; Barth et al., 2004; Pavet et al., 2005). In addition, AsA controls flowering time through phytohormones (Barth et al., 2004). Ascorbate can accumulate at millimolar concentrations in both photosynthetic and non-photosynthetic tissues (Foyer et al., 1983). This accumulation in such high quantities suggests that AsA is important for the plant as a major antioxidant.

1.4. The Ascorbate Metabolic Network

The biosynthetic pathway for vitamin C in animals was elucidated in the early 1950s and was proposed based on in vivo radio-labelling and feeding experiments in rats (Ishikawa et al., 2006). There is a single biosynthetic pathway for vitamin C in animals. Evidence obtained during the last 18 years indicates that there are four pathways that lead to the formation of AsA in plants. These routes are the D-mannose/L-galactose (Wheeler et al., 1998), L-gulose (Wolucka and Van Montagu 2003), D-galacturonate (Agius et al., 2003), and myo-inositol (Lorence et al., 2004) pathways. FIG. 2 shows this ascorbate metabolic network.

1.4.1. The D-Mannose/L-Galactose Pathway

It is commonly known as the "Smirnoff/Wheeler" pathway. All the genes involved in this route have been characterized. The starting precursor for this route is D-glucose, which is converted to GDP-D-mannose followed by L-galactose that leads to AsA production. D-Glucose-6-P is then converted to GDP-D-mannose by a series of steps catalyzed by fructose-6-P, D-mannose-6-P, and D-mannose-1-P, and that include the vtc1 mutant locus (GDP-mannose pyrophosphorylase). All of these enzymes have been cloned and characterized (Conklin et al., 1999; Qian et al., 2007; Maruta et al., 2008). The conversion of GDP-D-mannose to AsA comprises four steps: GDP-L-galactose, L-galactose-1-P (Laing et al., 2004), L-galactose (Gatzek et al., 2002) and L-galactono-1,4-lactone (Imai et al., 1998). The GDP-D-mannose to GDP-L-galactose reaction is catalyzed by GDP-D-mannose-3',5'-epimerase a.k.a. GME (Wolucka and Van Montagu, 2003). The vtc2 enzyme and its close homolog vtc5 convert GDP-L-galactose into L-galactose-1-P (Smirnoff et al., 2001; Dowdle et al., 2007; Linster et al., 2007). The L-galactose-1-phosphate phosphatase (locus vtc4 in Arabidopsis) converts L-galactose-1-P into L-galactose (Conklin et al., 2006). L-Galactose is oxidized at the C1-position by an L-galactose dehydrogenase (GalDH) present in the cytosol to L-galactono-1,4-lactone (Wheeler et al., 1998; Gatzek et al., 2002). All enzymes in this pathway are cytosolic except the last step involving the oxidation of galactono-1-4-lactone to AsA that is carried out by the mitochondrial L-galactono-1,4-lactone dehydrogenase (GLDH), (Østergaard et al., 1997; Imai et al., 1998).

1.4.2. The L-Gulose Pathway

The L-gulose pathway uses a similar precursor as the D-mannose/L-galactose to the branch point at GDP-D-mannose. GDP-D-mannose is then converted by the GME enzyme into GDP-L-gulose. It is proposed that GDP-L-gulose is converted to L-gulono-1,4-lactone and to AsA in three subsequent steps catalyzed by GDP-L-gulose pyrophosphatase, L-gulose-1-phosphate phosphatase, and L-gulose dehydrogenase respectively (Wolucka and Van Montagu, 2003). The only enzyme that has been characterized in this pathway is GME and it is known to be cytosolic.

1.4.3. The D-Galacturonic Acid Pathway

Observations made in ripening strawberries established that D-galacturonic acid and its methyl ester can be metabolized to form AsA (Mapson and Isherwood, 1956, Loewus and Kelly, 1961). In addition to these early observations the discovery of a D-galacturonic acid reductase (GalUR) gene from strawberry (Agius et al., 2003) provide the main evidence supporting this route. To date GalUR is the only enzyme identified in this route, which has been shown to be cytosolic (Agius et al., 2003).

1.4.4. The Myo-Inositol Pathway

Biochemical and molecular data indicate that myo-inositol can also be a precursor for the biosynthesis of AsA in Arabidopsis (Lorence et al., 2004). This pathway involves four enzymes, starting from the oxidation of myo-inositol to D-glucuronic acid and further reduction to L-gulonic acid and to L-gulono-1,4-lactone, and further oxidation to AsA. These conversions are catalyzed by myo-inositol oxygenase (MIOX), glucuronate reductase (GlcUR), gluconolactonase (GNL), and L-gulono-1,4-lactone oxidase (GulLO) respectively. The first two enzymes have already characterized by the Lorence Laboratory. Arabidopsis thaliana lines over-expressing MIOX and GulLO are tolerant to multiple abiotic stresses such as salt, cold, heat, and pyrene (Lisko et al., 2013). These high expressing AsA plants exhibit increased growth and biomass accumulation (Lorence et al., 2004; Lorence and Nessler, 2007; Lisko et al., 2013).

Transgenic rice overexpressing MIOX showed improved growth performance when grown in the presence of 200 mM mannitol and presented higher survival rates compared to wild type plants treated with polyethylene glycol (Duan et al., 2012). MIOX proteins are present in almost all multicellular eukaryotes and are highly conserved across phyla. It has been reported that the role of MIOX and D-GlcUA for AsA biosynthesis in plants is a major plant antioxidant to counterbalance oxidative damage (Shao et al., 2008). The first two enzymes in the inositol pathway to AsA are cytosolic. The Lorence laboratory has evidence indicating that some isoforms of the last two enzymes in this pathway reside in the chloroplast and the endoplasmic reticulum (ER).

1.5. Role of Ascorbate in the Chloroplast

Chloroplasts are the organelles responsible for photosynthesis, a process that is essential for plant growth and development (Rustchow et al., 2008; Venkatasalam, 2012). Key metabolites in the photosynthetic process are NADPH and ATP. Although photosynthesis is an essential process, light absorption creates oxidative stress due to the formation ROS, such as singlet oxygen ($^1O_2$), superoxide ($O_2^-$) and hydrogen peroxide ($H_2O_2$) (Oelze et al., 2008). Under high light, the electron flow through the photosynthetic chain overcomes the passage of electrons from ferredoxin to several reductases, and this causes an over-reduction of the plastoquinone and cytochrome b complex. Thus, during a day with high irradiance, plants are under constant oxidative stress (Oelze et al., 2008). Light/dark cycles are probably the most important signals that regulate plant development. Light is essential for photosynthesis, but an excess inside the chloroplast leads to excessive ROS. Among the chief defense mechanisms that allow plants to cope with environmental stress situations is the ascorbate-glutathione cycle, a complex metabolic pathway in which a variety of photochemical and enzymatic steps are involved. Ascorbate is essential to detoxify $H_2O_2$ produced during the Mehler reaction, which is formed by dismutation of $O_2^-$ and can be regenerated via the AsA-glutathione cycle to counteract $O_2^-$ (Halliwell and Foyer, 1976; Foyer and Noctor, 2000; Munné-Bosch and Alegre, 2002; Talla et al., 2011). FIG. 3 shows the Anti-oxidation of reactive oxygen species. Reactive oxygen is generated when electrons (e–) not utilized in photosynthesis are donated to oxygen, thus creating superoxide (O2.–) that can be converted to hydrogen peroxide (H2O2) by superoxide dismutase (SOD). The H2O2 is further converted to H2O by ascorbate peroxidase (APX) utilizing ascorbate (AsA) as an electron donor that, in turn, becomes oxidized ascorbate (ox-AsA). Additional electrons are consumed via the conversion of ox-AsA back to AsA or the conversion of double ox-AsA back to AsA using glutathione. The resulting oxidized glutathione is reduced by electrons from electron transport by means of glutathione reductase (GR). Source: Demmig-Adams et al., 2012. The demand for AsA in these reactions increases at higher light intensities, when formation of ROS is enhanced. Experimental evidence suggests the existence of an effective signaling network between the chloroplast and the mitochondria that involves ROS and antioxidants (Foyer and Noctor, 2003; Noctor et al., 2007). The different light/dark conditions are currently one of the major challenges in plant research to improve crop productivity under a changing global climate.

Ascorbate is present in all plants although its concentration varies greatly and has been identified in various compartments of the cell. Ascorbate occurs inside as well as outside the chloroplast (Constable, 1963; Hall and Rao, 1999, Habermann, 2013), where it has been shown to accumulate at concentrations up to 50 mM (Hall and Rao, 1999); this represents about 25-30% of the total AsA in the plant cell (Horemans et al., 2000). All known AsA biosynthetic enzymes reside in compartments other than the chloroplast, and therefore it is currently unknown how this organelle is able to accumulate such high concentrations of this antioxidant.

Ascorbate was at one time considered to be a necessary component of the photosynthetic phosphorylation system (Arnon, 1959) however is now considered important in providing a protective role in preventing inactivation of essential components of the chloroplasts (Pintó-Marijuan and Munné-Bosch, 2014).

It has been recognized for more than a century that chloroplasts alter their distribution within cells depending on the external light conditions. Chloroplasts can be observed to move to positions that maximize photon absorption under low-influence light and, conversely, to move to positions that minimize photon absorption under high light. The movement away from areas of strong light is believed to offer areas of strong light protection against photo-oxidative damage (Eckardt, 2003).

Arabidopsis plants growing under long day conditions (12 h of photoperiod) accelerate flowering in comparison with plants growing under shorter photoperiods. Short days distinctly extend the vegetative phase of Arabidopsis growth and delay senescence (Lepistö and Rintamäki, 2012). In the course of high-light acclimation, elevated ROS production is compensated for by induction of antioxidant systems in leaves which in turn prevent the oxidation of leaf cells (Mittler et al., 2004).

1.6. Definition of the Problem

Significant progress has been made in the characterization of myo-inositol oxygenase (MIOX) and glucuronate reductase (GlcUR), the first two enzymes of the myo-inositol pathway to AsA (Lorence et al., 2004; Lorence and Nessler, 2007). High AsA lines over-expressing MIOX4 and GuILO are tolerant to multiple causes of oxidative stress including salt, cold, heat, and pollutants (Lisko et al., 2013). The third enzyme, GNL, has been characterized in rat, Zymomonas mobilis, and Pseudomonas aeruginosa (Tarighi et al., 2008), but not in plants. Current research in the Lorence Group focuses on the characterization of this third enzyme. Preliminary data indicate the presence of isoforms of glucuronolactonase (GNL) that are targeted to the ER and the chloroplasts. This project focuses on gaining insights about the function of a putative GNL that possesses a chloroplastic signal peptide. This is quite relevant as it is currently unknown how this organelle that makes photosynthesis possible, is able to accumulate up to 50 mM AsA.

1.7. Hypothesis and Aims for the Role of Ascorbate in the Chloroplast

If At1g56500 encodes a functional glucuronolactonase (GNL) that resides in the chloroplast, then this protein will protect this organelle and green tissues, and will counteract reactive oxygen species formed under light stress. When over-expressed in plants this enzyme will confer plants enhanced photosynthetic efficiency.

This hypothesis will be tested by addressing the following aims:

Aim 1: Characterize the AtGNL (At1g56500) functional enzyme.

Aim 2: Establish the role of the AtGNL under low, normal, and high light conditions.

Aim 3: Characterize the phenotype and photosynthetic efficiency of Arabidopsis lines with low, normal, and high AtGNL expression.

II. Description of the Known Art

Patents, patent applications, and references disclosing relevant information are disclosed below. These patents, patent applications, and references are hereby expressly incorporated by reference in their entirety.

SUMMARY OF THE INVENTION

Chloroplasts, the organelles responsible for photosynthesis, are essential for plant growth and development, and are involved in the metabolism of carbon, nitrogen, and sulfur (Venkatasalam, 2012; Rustchow et al., 2008). In addition, chloroplasts synthesize amino acids, fatty acids, purine, and pyrimidine bases, isoprenoids, tetrapyrroles, and the lipid components of their own membranes, followed by processing, folding, and assembly by various chaperone systems (Peltier et al., 2006). The chloroplasts need considerable protein import from the cytosol. Chloroplasts control nuclear gene expression indirectly by metabolites, ROS and other cellular processes (Pogson et al., 2008; Pfannschmidtm, 2010).

It has been recognized for more than a century that chloroplasts alter their distribution within cells depending on the external light conditions. Chloroplasts can be observed to move to positions that maximize photon absorption under low light and, conversely, to move to positions that minimize photon absorption under high light. The movement away from areas of strong light is believed to offer protection against photo-oxidative damage (Eckardt, 2003). The photoreceptors responsible for light induced chloroplast movement in higher plants are phototropins. The phototropins PHOT1 and PHOT2 are involved in blue light mediated chloroplast relocation, stomatal opening and phototropism (Briggs and Christie, 2002). PHOT1 is the primary photoreceptor that controls phototropism in low light (Huala et al., 1997), whereas PHOT2 is responsible for the light-avoidance relocation of chloroplast under high light (Kagawa et al., 2001).

Ascorbate (AsA) is found in all plants although its concentrations vary greatly. Within the leaf, ascorbate occurs inside as well as outside the chloroplasts (Constable, 1963; Habermann, 2013). Ascorbate was at one time considered to be a necessary component of the photosynthetic phosphorylation system but recently it has been regarded as having a protective role in preventing inactivation of essential components of the chloroplasts (Arnon, 1959; Pintó-Marijuan and Munné-Bosch, 2014). Ascorbate helps detoxify $H_2O_2$ produced during the Mehler reaction, (Foyer and Noctor 2000; Talla et al., 2011) and is important for photoprotection (Demmig-Adams et al., 2012). In chloroplasts, high ascorbate levels are required to overcome photoinhibition caused by strong light (Miyaji et al., 2014).

The myo-inositol pathway is one of the four routes for the production of AsA in plants. This pathway has not been completely elucidated. Three enzymes have been characterized: myo-inositol oxygenase (MIOX), glucuronate reductase (GlcUR), and L-gulono-1,4-lactose oxidase (GuTLO) (Lorence et al., 2004; Lorence and Nessler, 2007, Lisko et al., 2013; Aboobucker, 2014). The third enzyme, gluconolactonase (GNL), has been characterized in *Rattus norvegicus* (Kondo et al., 2006), *Euglena gracilis* (Ishikawa et al., 2008), *Pseudomonas aeruginosa* (Tarighi et al., 2008), *Xanthomonas campestri* (Chen et al., 2008), *Homo sapiens* (Aizawa et al., 2013), and *Gluconobacter oxydans* (Shinagawa et al., 2009), but not in plants.

The first two enzymes in this pathway (MIOX4 and GlcUR) are cytosolic, the fourth enzyme (GuILO) resides in the ER as illustrated in FIG. 4. FIG. 4 shows the Subcellular localization of enzymes in the ascorbate metabolic network. GLDH, the terminal enzyme in the D-mannose/L-galactose pathway is located in the mitochondria, while the terminal enzyme in the myo-inositol and L-gulose routes (GulLO) is known to reside in the endoplasmic reticulum. All other enzymes are supposed to be cytoplasmic. However, the localization of the third enzyme (GNL) is unknown. In 2004 gene sequences of well characterized GNLs from rat and bacteria were aligned and compared to the *Arabidopsis* genome (A. Lorence, personal communication). This resulted in the identification of 18 putative GNL candidate genes. FIG. 5 shows the Putative glucuronolactonases (GNLs) in *Arabidopsis*. The T-DNA knockouts were screened looking for low AsA lines to identify true GNLs in *Arabidopsis*. The foliar AsA content in knockout lines corresponding to the GNL *Arabidopsis* genes were measured to identify low AsA mutants. Bioinformatics analysis of the genes found that one of the SALK lines with low AsA encodes a protein that possesses a chloroplastic signal peptide. In addition, microarray data available at Genevestigator (Zimmermann et al., 2004) showed that there is a suppression of the expression of this gene (At1g56500) when plants are exposed to dark conditions. To understand the role of AtGNL in plant physiology, two knockout lines with a T-DNA inserted into the At1g56500 gene were obtained from the *Arabidopsis* Biological Resource Center (ABRC). FIG. 6 shows the Schematic of the insertion site of the T-DNA in the At1g565400 gene in SALK lines 026172 and 011623 (red squares). Exons are shown as blue boxes. Source: TAIR database.

The At1g56500 cDNA was amplified and sub-cloned into the pBIB-Kan vector under the control of the cauliflower mosaic virus 35S promoter and the tobacco etch virus (TEV) enhancer. A 6×-HIS tag was added at the 5' end of the cDNA to facilitate protein detection by Western blot and purification by nickel affinity chromatography.

To confirm that indeed this gene encodes a protein residing in the chloroplast, the *Nicotiana benthamiana* was infiltrated with an AtGNL construct using an optimized *Agrobacterium*-mediated transient transformation method (Medrano et al., 2009). Chloroplasts were isolated from leaves using a chloroplast isolation kit (CP-ISO Sigma). A Western blot developed with an anti-HIS antibody, confirmed that AtGNL is indeed in the chloroplast as illustrated in FIG. 7. FIG. 7 shows the AtGNL protein resides in the chloroplast. Chloroplasts were isolated from leaves of *Nicotiana benthamiana* plants infiltrated with the AtGNL construct using a chloroplast isolation kit (CP-ISO, Sigma). Western blot was done using an anti-HIS antibody. M: molecular weight marker, lane 1 empty vector fraction, lane 2 non chloroplastic fraction, lane 3 chloroplastic fraction, lane 4 chloroplast fraction after purification by nickel affinity chromatography.

This work focuses on characterizing a functional At1g56500 (AtGNL). In this work three aims are proposed: Aim 1: Characterize the AtGNL (At1g56500) functional enzyme, Aim 2: Establish the role of the AtGNL under low, normal, and high light conditions, and Aim 3: Characterize the phenotype and photosynthetic efficiency of *Arabidopsis* lines with low, normal, and high AtGNL expression.

Vitamin C (L-ascorbic acid, AsA) is the most abundant water-soluble antioxidant in plants. Ascorbate scavenges free radicals, is an enzyme cofactor, and a donor/acceptor of electrons in the chloroplast. Ascorbate protects tissues against damage caused by reactive oxygen species (ROS) produced through normal metabolism or generated from stress. The inositol route to AsA involves four enzymes: myo-inositol oxygenase, glucuronate reductase, gluconolactonase (GNL), and L-gulono-1,4-lactone oxidase (GulLO). The third enzyme, GNL, has been characterized in rat and bacteria but not in plants. Eighteen putative GNLs were identified in *Arabidopsis*, one of which, AtGNL, is interesting because it possesses a chloroplastic signal peptide. Chloroplasts can accumulate up to 50 mM AsA but until now no chloroplastic AsA biosynthetic genes have been described. This study includes the characterization of the first plant GNL enzyme in vitro and in planta. Knockouts on this gene had lower foliar AsA and stunted growth compared to controls. The functional gene restored the phenotype of the knockouts, and those plants had higher AsA content, and enhanced photosynthetic capacity. These results highlight the importance of AtGNL in AsA formation and in maintaining a healthy redox balance in the leaves particularly under low light stress. AtGNL is the first AsA biosynthetic enzyme that resides in chloroplasts.

Accordingly, it is an object of the present invention to characterize the AtGNL (At1g56500) functional enzyme.

It is another object of the present invention to establish the role of the AtGNL under low, normal, and high light conditions.

It is another object of the present invention to characterize the phenotype and photosynthetic efficiency of *Arabidopsis* lines with low, normal, and high AtGNL expression.

It is another object of the present invention to increase photosynthetic efficiency.

It is another object of the present invention to increase AtGNL expression.

It is another object of the present invention to provide a method for a purification protocol for AtGNL recombinant protein.

It is another object of the present invention to increase the levels of AsA within a plant.

It is another object of the present invention to increase the biomass of the plants.

It is another object of the present invention to delay aging of the plants.

It is another object of the present invention to increase production of ATP.

These and other objects and advantages of the present invention, along with features of novelty appurtenant thereto, will appear or become apparent in the course of the following descriptive sections and the attached drawings.

BRIEF DESCRIPTION OF THE DRAWINGS

In the following drawings, which form a part of the specification and which are to be construed in conjunction therewith, and in which like reference numerals have been employed throughout wherever possible to indicate like parts in the various views:

FIG. 1 is a chemical structure view of one embodiment of the present invention;
FIG. 5 is a table view thereof;
FIG. 8 is a construct view thereof;
FIG. 9 is a table view thereof;
FIG. 12 is an analytical view thereof;
FIG. 13 is a table view thereof;
FIG. 14 is a graph view thereof;
FIG. 15 is a graph view thereof;
FIG. 16 is a graph view thereof;
FIG. 17 is a table view thereof;
FIG. 18 is a graph view thereof;
FIG. 19 is a photographic and chart view thereof;
FIG. 21 is a chart view thereof;
FIG. 22 is a table view thereof;
FIG. 23 is a chart view thereof;
FIG. 26 is a chart view thereof;
FIG. 27 is a table view thereof;
FIG. 28 is a chart view thereof;
FIG. 29 is a table view thereof;
FIG. 30 is a chart view thereof;
FIG. 31 is a table view thereof;
FIGS. 34A and 34B are table views thereof;
FIGS. 36A, 36B, and 36C are a genetic sequencing view of one embodiment of the present invention (SEQ ID NO: 1);
and
FIG. 37 is a genetic sequencing view of one embodiment of the present invention (SEQ ID NO: 2).

DETAILED DESCRIPTION

Figure 2:
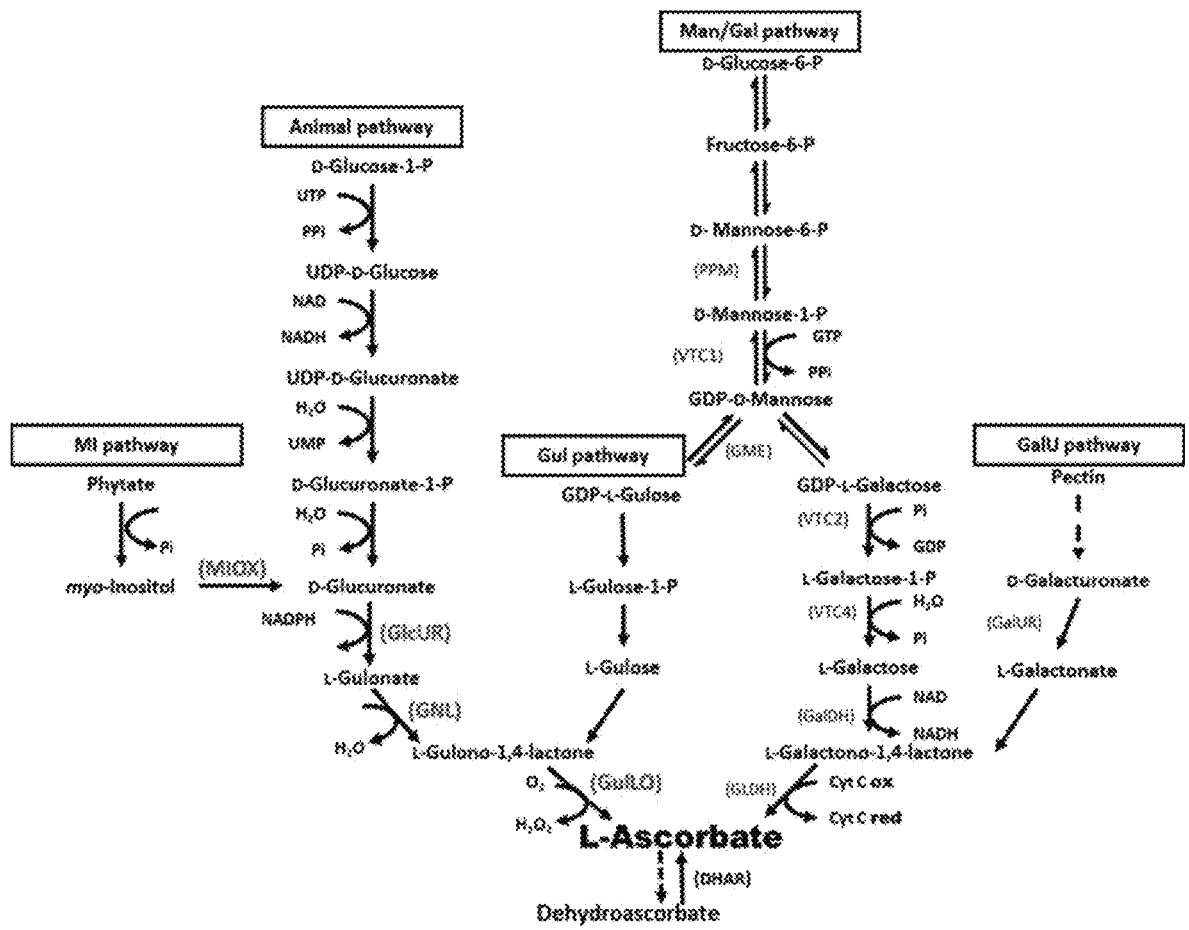
FIG. 2 is a metabolic network view thereof.
Figure 3:
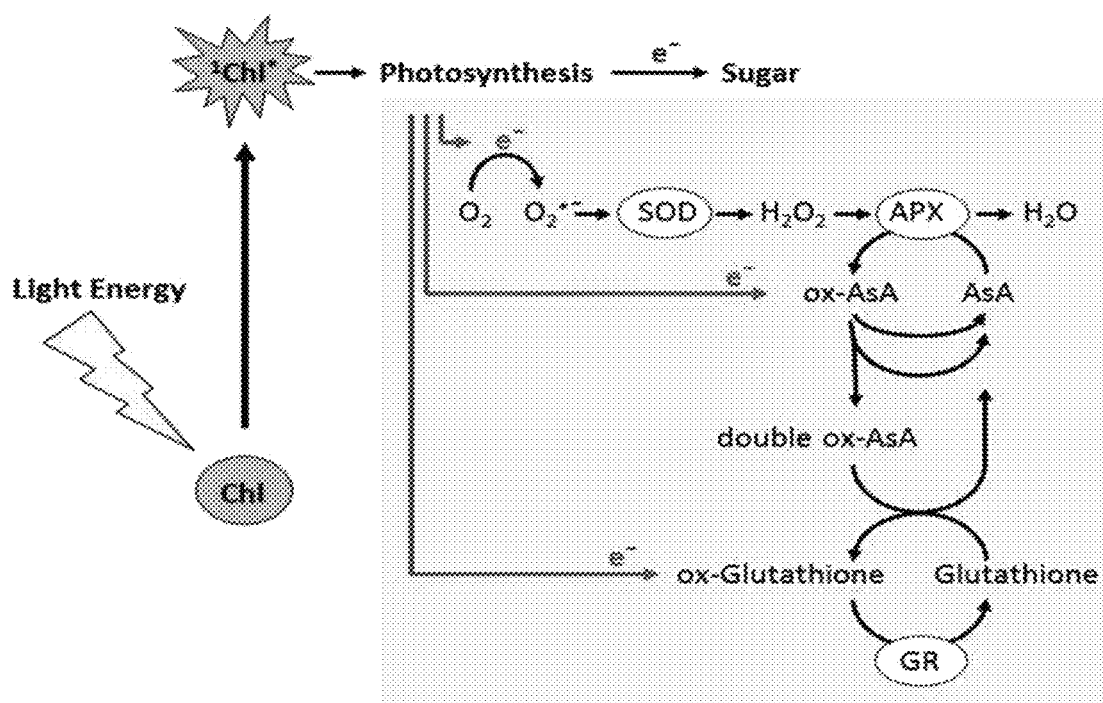
FIG. 3 is a flowchart view thereof.
Figure 4:
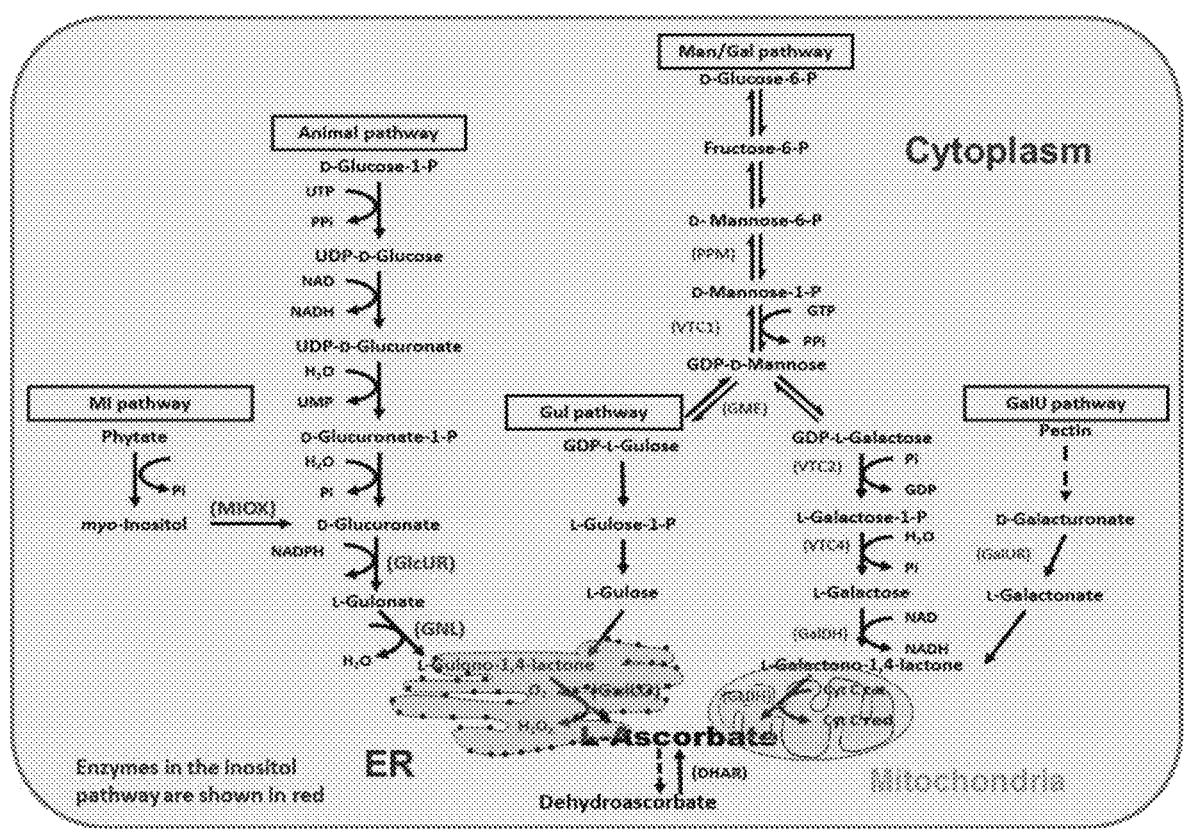
FIG. 4 is a metabolic network view thereof.
Figure 6:
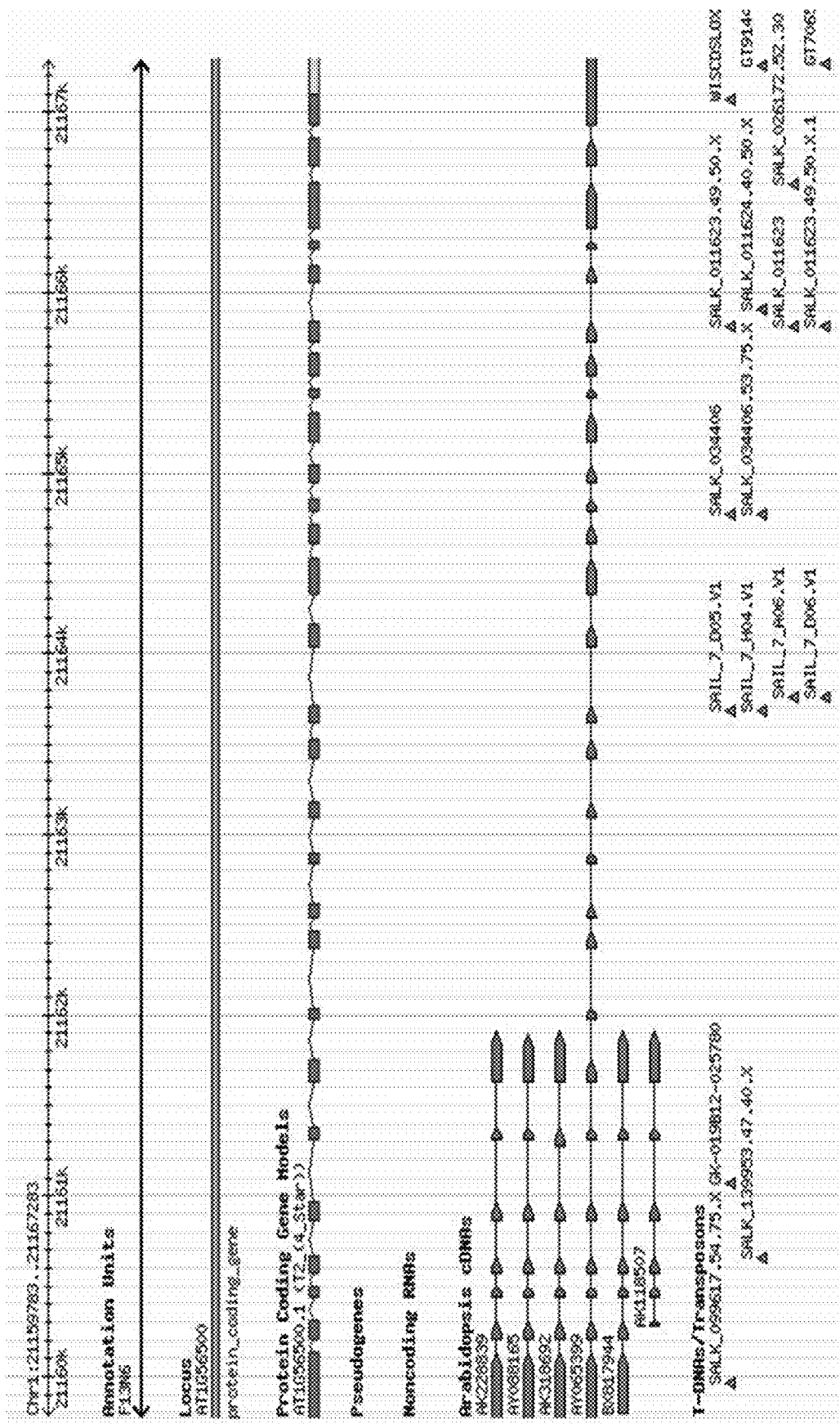
FIG. 6 is a schematic view thereof.

*Arabidopsis thaliana* ecotype Columbia wild type seeds (Col-0, stock #CS60000), SALK_026172, and SALK_011623 were obtained from the *Arabidopsis* Biological Resource Center (ABRC, Columbus, Ohio). Seeds were sterilized with 70% (v/v) ethanol for 10 min followed by 50% (v/v) sodium hypochlorite containing 0.05% (v/v) Tween-20 for 15 min. Next, seeds were washed 6 times with sterile water. Finally, seeds were transferred to a petri dish containing medium which consisted of Murashige-Skoog (MS) salts (Murashige and Skoog, 1962), MS vitamins, and 3% (w/v) sucrose, at pH 5.6. The medium was supplemented with 0.04% (w/v) $MgSO_4 \cdot 7H_2O$. The seeds were vernalized for 3 days at 4° C. Plates were transferred to a growth chamber and incubated at 23° C., 65% humidity, 16:8 h photoperiod and 200 $\mu mol/m^2/s$ light intensity. After establishment, seedlings were transferred to PM-15-13 AIS MIX *Arabidopsis* soil (Lehle-Seeds, Round Rock, Tex.) in 2 inch pots. Pots were covered with a dome for one week and after that plants were grown until they reached maturity.

*Nicotiana benthamiana* seeds were obtained from The Department of Plant Pathology, Physiology and Weed Science at Virginia Polytechnic Institute and State University (Blacksburg, Va.). Seeds were sown in 4.5 inch pots containing Pro-mix BX soil (Premier Horticulture Ltd, Canada) with fertilizer Osmocote 14-14-14 (Scotts, Canada). Vermiculite was overlaid on top of the seeds. The pots were covered with a dome for one week. Plants were grown in an environmental control chamber with the following conditions: 25° C. (day)/21° C. (night) temperature, 65% relative humidity, 16:8 h photoperiod, and 150 $\mu mol/m^2/s$ light intensity.

2.2.2. Constructs of Interest

Two gene constructs were made for this project. The first construct is one where the cDNA encoding a putative AtGNL was placed under the control of the 35S promoter and the tobacco etch virus (TEV) enhancer (AtGNL-6×HIS: pBIB-Kan), (Becker, 1990). In this construct a histidine tag was added to the C-terminus of the protein of interest to allow detection using antibodies and to facilitate purification. The second construct is one where the putative promoter region of the AtGNL (a 1000 bp fragment preceding the ATG) was cloned and fused to the GUS reporter gene to better understand the spatial and temporal expression of this gene (pAtGNL:pCAMBIA1305.1). FIG. 8 shows the Constructs of interest. (A) The At1g56500-HIS:pBIB-Kan construct containing At1g56500 (AtGNL) with a six histidine (6×-HIS) tag and adjacent neomycin phosphotransferase II (nptII) selectable marker. (B) The pAt1g56500:pCAMBIA1305.1 construct containing the AtGNL promoter with the GUS-PLUS reporter gene and the hygromycin phosphotransferase (hph) selectable marker. NOS-P: promoter of nopaline synthase gene, 35S-T: terminator of the 35S cauliflower mosaic virus gene; TEV: tobacco etch virus translational enhancer; LB and RB: left and right T-DNA borders, respectively.

2.2.3. Development of Transgenic Lines

To study the expression of AtGNL in *Arabidopsis thaliana*, stable transgenic plants were developed by the floral dip method (Clough and Bent, 1998). Wild type CS60000 and knockouts: SALK_026172 and SALK_011623, were transformed with the *Agrobacterium tumefaciens* GV3101 strain carrying the construct of interest. The T0 seeds were planted on MS medium plus kanamycin. The antibiotic resistant seedlings were transferred to soil and grown to maturity under the above stated conditions. The presence of the transgene of interest was established via PCR using gene specific primers, and genomic cDNA as a template. To develop homozygous versions of the knockout lines, overexpresser (wild type plus AtGNL), and restored lines (knockouts plus AtGNL) T1 plants that were high AsA expressers were identified. The seeds of those plants were sterilized with 70% (v/v) ethanol for 10 min followed by 50% (v/v) sodium hypochlorite containing 0.05% (v/v) Tween-20 for 15 min. Next, seeds were washed 6 times with sterile water. Finally, seeds were transferred to petri dishes containing Murashige and Skoog (MS) medium which consists of salts, MS vitamins, and 3% (w/v) sucrose at pH 5.6. The medium was supplemented with 0.04% (w/v) $MgSO_4 \cdot 7H_2O$, and 50 mg/L kanamycin. Plated seeds were vernalized for 3 days at 4° C. After establishment, seedlings were transferred to soil and grown under the above stated conditions until they reached maturity. This process was repeated until plants with a 100% germination score in the presence of antibiotic selection were developed.

2.2.4. Ascorbate Measurements

In *Arabidopsis*, in planta AsA concentration changes throughout the day as well as during development (Tamaoki et al., 2003; Zhang et al., 2009). Fifty mg of leaf tissue were collected between 9:00 am and 11:00 am. Tissue was frozen immediately in liquid nitrogen and stored at −80° C. until analyzed. Reduced, oxidized, and total AsA were measured using a 96-well plate format as described by Haroldsen et al., (2011). Briefly, frozen tissue was pulverized in 6% (w/v) meta-phosphoric acid, and centrifuged at 13,000 rpm for 15 min. Reduced AsA was determined by measuring the decrease in absorbance at 265 nm after addition of 0.5 unit of ascorbate oxidase to 300 μL of the reaction medium containing the plant extract and 100 mM phosphate buffer at pH 6.9. Oxidized ascorbate was measured in a 300 μL reaction mixture with 10 μL of 40 mM dithiothreitol (DTT) after incubation in the dark for 20 min at room temperature. The reaction was followed by measuring absorption at 265 nm. Calculations were made based on a standard curve made with pure L-ascorbic acid run in parallel. Ten biological replicates were measured in analytical triplicate and reported as μmol per gram fresh weight (μmol/g FW).

2.2.5. Transient Expression of AtGNL in *Nicotiana benthamiana*

In order to test its function the putative GNL recombinant protein was produced in *Nicotiana benthamiana*. This plant is a widely used platform for the production of active proteins, including antibodies, enzymes and other proteins that require post-translational modifications (Klimyuk et al., 2012; Leuzinger et al., 2013). To find the optimal expression time, five week old *N. benthamiana* plants were vacuum infiltrated with the At1g56500-6×HIS.pBIB-kan construct as described by Medrano et al., 2009. Leaf tissue was harvested at 24, 48, 72, and 96 h post infiltration for further analysis. The optimum time for tissue collection based on Western blot data, was found to be at 48 h post infiltration (data not shown). In subsequent experiments all leaves were collected at 48 h post-infiltration, frozen immediately in liquid nitrogen and stored at −80° C. until further processing. Plants infiltrated with the empty pBIB-kan binary vector (EV) were used as controls for these experiments.

In order to confirm the expression of the AtGNL in *N. benthamiana*, Western blot experiments were carried out. Crude extracts were made by grinding frozen tissue in the presence of two volumes of SDS buffer containing 150 mM Tris-HCl pH 6.8, 5 mM EDTA pH 8.0, 30% (v/v) glycerol, 6% (w/v) SDS. The homogenate extract was then centrifuged at 13,000×g for 15 min, and the supernatant was recovered. Proteins were separated via SDS-PAGE. Six L of plant extract were mixed with 2.5 μL of SDS loading buffer (4×) and 1 μL of DTT, incubated for 10 min at 70° C. and separated by SDS-PAGE on 10% precast mini-gels (Expedeon, San Diego, Calif.) with a Tris-MOPS buffer. Subsequently, separated proteins were electro blotted onto a nitrocellulose membrane, using transblotting buffer containing: 25 mM Tris base, 192 mM glycine, and 20% methanol. Recombinant AtGNL-6×HIS was detected using an anti-HIS (C-term)/AP antibody at a 1:2,000 v/v dilution (Invitrogen, Carlsbad, Calif.) and CDP-start, a chemiluminescent substrate for alkaline phosphatase detection (Roche Diagnostics, Indianapolis, Ind.).

2.2.6. Recombinant AtGNL Purification

Recombinant AtGNL protein was purified from *N. benthamiana* leaves. Five grams of leaf tissue were pulverized in liquid nitrogen and proteins were extracted with 10 mL of buffer A (75 mM sodium phosphate dibasic, 25 mM sodium phosphate monobasic, 150 mM NaCl, 10 mM sodium metabisulfite, and 0.6% (v/v) protease inhibitor cocktail, pH 7.4). The extract was then centrifuged at 13,000×g for 15 min. The supernatant obtained after centrifugation was loaded onto a nickel affinity column (HIS60 Ni Superflow) and incubated for 1 h at 4° C. Then, the column was washed with 50 mM sodium phosphate pH 7.4, 300 mM NaCl, 40 mM imidazole buffer and the bound proteins were eluted with 250 mM of imidazole. The eluate from the nickel column was concentrated using an AMICON® 30K ultra centrifugal filter (Millipore, Billerica, Mass.). Total soluble protein concentration was estimated by the Bradford method (Bradford, 1976) using Coomassie blue G-250 dye (Thermo Scientific) and bovine serum albumin (Pierce, Rockford, Ill.) as a standard. Protein fractions from the purification procedure were separated by SDS-PAGE and the AtGNL was detected by Western blot and silver staining using Pierce® Silver Stain Kit (Thermo Scientific).

2.2.7. Recombinant AtGNL Enzyme Assay

The lactonase activity was assayed in vitro based on the decrease in absorbance (405 nm) of the p-nitrophenol pH indicator that resulted from the enzymatic opening of the lactone ring when D-glucono-δ-lactone was used as substrate in the presence of the AtGNL as previously described (Ishikawa et al., 2008). Enzyme preparations were made fresh for individual experiments at room temperature.

In order to establish the optimal enzyme activity for AtGNL, several conditions were tested. The optimum concentration for enzyme activity was 30 μg per reaction. One mL of the reaction typically contained: 10 mM PIPES pH 6.5, 5 mM D-glucono-δ-lactone, 75 μM $MnCl_2$, 2.5 mM p-nitrophenol, and an aliquot of the purified enzyme. An equal amount of boiled enzyme was used as control for these experiments.

In order to examine the specificity of the AtGNL enzyme for D-glucono-δ-lactone, multiple substrates were tested in the lactonase assay. The substrates used in this experiment were: D-glucono-δ-lactone (D-GuIL), L-galactono-γ-lactone (L-GaIL), L-galactonic acid (L-GalA), L-gulono-γ-lactone (L-GuIL), and L-gulonic acid (L-GulA). The L-GalA and L-GuIA were prepared by the hydrolysis of L-GaIL and L-GuIL, respectively. For hydrolysis 20 mL of 0.3 M NaOH were added to 100 μL of 10 mM L-GalL or L-GuIL, the mixture was vigorously agitated by vortexing for 20 s, and 20 μL of 0.3 M HCl were added to neutralize the solution (Ishikawa et al., 2008). For enzyme kinetic experiments, individual reactions were monitored for 15 min at different substrate concentrations. Analysis was done using the GraphPadPrism 6.2 software.

2.2.8. High Throughput Phenotyping

To characterize the phenotype of the over-expresser (L60, L61, L62), knockout lines (SALK_026172 and SALK_011623), and restored lines (L89, L90, L100, L128, L129, L130), under low, normal, and high light conditions a high throughput phenotyping platform (Scanalyzer HTS instrument, Lemnatec, Germany) and the LemnaControl software were used. This instrument is equipped with a robotic arm that holds visible (VIS, a.k.a. RGB), fluorescence (FLUO), and near infrared (NIR) high-resolution cameras. This system empowers unbiased, non-invasive, automated, and effective characterization of plant phenotypes. The cameras in the system are as follows: VIS camera, piA2400-17gc CCD (Basler, Ahrensburg, Germany) with resolution of 2454×2056 pixels; FLUO camera, scA1600-14gc CCD (Basler, Ahrensburg, Germany) with resolution 1624×1234 pixels; and NIR camera, Goldeye GIGE P-008 SWIR (Allied Vision Technologies, Stadtroda, Germany) with resolution 320×256 pixels and with spectral sensitivity between 900 and 1700 nm.

In the greenhouse plants were grown in PM-15-13 AIS MIX soil (Lehle-Seeds, Round Rock, Tex.) in Quickpot 15 trays in a greenhouse during Mar. 12-30, 2015 in Jonesboro, Ark., USA (latitude 29.4889 and longitude −98.3987). Growth conditions were as follows: 22° C.-26° C. temperature, 16:8 h photoperiod, 55% humidity and three different light conditions: low (35-110 $\mu mol/m^2/s$), medium (110-350 $\mu mol/m^2/s$) and high light (350-700 $\mu mol/m^2/s$). Light intensity was recorded four times per day (9:00 am, 12:00 pm, 3:00 pm, and 6:00 pm) to cover the entire sunlight period.

Images of AtGNL lines were captured every two days between 16 days and 26 days after germination, to cover the full vegetative growth. Images (5670 images=7 lines×15 biological replicates×3 light treatment×6 times points×3 cameras) were analyzed using the LemnaGrid Software. The analysis of the RGB images was done as previously described by Arvidsson et al., (2011). Multiple phenotypic parameters were calculated for each plant including: projected leaf area ($cm^2$), convex hull area ($cm^2$), caliper length (a.k.a. rosette diameter, mm) and compactness (measure of the bushiness of the plant). From the RGB images the relative area of the plants displaying normal green color versus the area with detectable yellow color (chlorosis) were calculated. The analysis of the NIR images was similar to the color classification of VIS camera, using the acquired grayscale images, where high water content corresponds to darker tones while low water corresponds to lighter gray tones. The software used this information to calculate the relative area with low, medium, and high water content. The fluorescence camera acquires red-scale images and in this case the red tones were divided into four equidistant bins, and the software calculated the relative area with zero, low, medium, and high fluorescence. Quantitative data obtained from the images were analyzed.

2.2.9. Photosynthetic Efficiency

In order to determine photosynthetic efficiency of photosystem II ($\Phi/II$), linear electron flow (LEF), and non-photochemical quenching (NPQt) of the knockout lines (SALK_026172 and SALK_011623), over-expresser (L61), restored lines (L100 and L129), empty vector, and wild type controls growing under low and normal light conditions were analyzed using a MultispeQ. This is a hand held fluorometer developed by the Kramer Laboratory at Michigan State University. Ten biological replicates were chosen randomly at the same time of day for measurements. Data were visualized in an Android tablet (Samsung Galaxy Tab 4) and analyzed in the PhotosynQ website (www.photosynq.org).

2.2.10. PromoterAtGNL:GUS Expression in *Arabidopsis thaliana*

To study the expression of At1g56500 in different plant tissues, *Arabidopsis thaliana* var. Columbia was transformed by the floral dip method (Clough and Bent, 1998) with *Agrobacterium tumefaciens* GV3101 carrying the construct of interest (pAtGNL:pCAMBIA1305.1). A different set of plants was also transformed with bacteria carrying the empty vector control (pCAMBIA1305.1). T0 seeds were selected with hygromycin and the antibiotic resistant seedlings were transferred to soil and grown to maturity under the above mentioned conditions. The presence of the transgene of interest was established via PCR using gene specific primers, and genomic cDNA as a template. Seeds of the PCR positive plants were sterilized and transferred to a petri dish containing MS media with 20 mg/L hygromycin. Plated seeds were vernalized for 3 days at 4° C. and then transferred to an environmentally controlled chamber. Hygromycin resistant seedlings were transferred to soil and grown until maturity.

Explants (seedlings, leaves, flowers, and fruits) were cut from plants 4, 8, 12, and 30 days after germination. Next, the explants were incubated in fresh and cold phosphate buffer pH 7.0 with 4% formaldehyde at room temperature for 30 min. The explants were washed several times with cold phosphate buffer for 1 h, then vacuum infiltrated with X-Gluc substrate solution containing: 1 mg 5-bromo-4-chloro-3-indolyl β-D-glucuronide in 100 µL of methanol, 1 mL 2× phosphate buffer, 20 µL 0.1 M potassium ferrocyanide, 20 µL 0.1 M potassium ferricyanide, 10 µL 10% (w/v) solution of Triton X-100, and 850 µL of water. Tissues were incubated in darkness at room temperature overnight until a distinct blue staining appeared. Finally, explants were incubated in 70% ethanol until the chlorophyll was removed. Photographs were taken with AxioCam MRc camera connected to a Stemi 2000-C stereo microscope (Zeiss).

2.2.11. Phylogeny

In order to identify a functional GNL in *Arabidopsis thaliana* (AtGNL), known GNLs, and putative GNLs from other organisms were compared using the TAIR database (www.arabidopsis.org). The AtGNL was obtained from TAIR database based on highest protein homolog. That sequence was then converted to FASTA format using the EMBL-EBI (www.ebi.ac.uk/tools/stc/readseq/). The MEGA6 software enabled reading and comparing the AtGNL with known and putative GNL sequences (Tamura et al., 2013).

2.2.12. Statistical Analysis

Data was analyzed by SAS software 9.4 (SAS Institute, 2016). Analysis of variance was carried out by ANOVA procedure. Least squares means (LS-means) were calculated to evaluate AsA content per line, at $\alpha=0.05$.

2.3. Results and Discussion 2.3.1. Purification and Characterization of Recombinant At1g56500

To demonstrate the GNL activity of *Arabidopsis thaliana* gluconolactonase in vitro, an *N. benthamiana*-based transient expression system was used. Plants were vacuum infiltrated with the *Agrobacterium tumefaciens* LBA4404 strain carrying the At1g56500-6×HIS construct. The protein accumulation is highest at 48 h post infiltration (data not shown).

In order to establish a protein purification protocol for AtGNL, several extraction buffers were tested to identify those that allow recovery of the highest amount of protein. FIG. 9 shows the list of buffers tested for protein purification.

Figure 7:
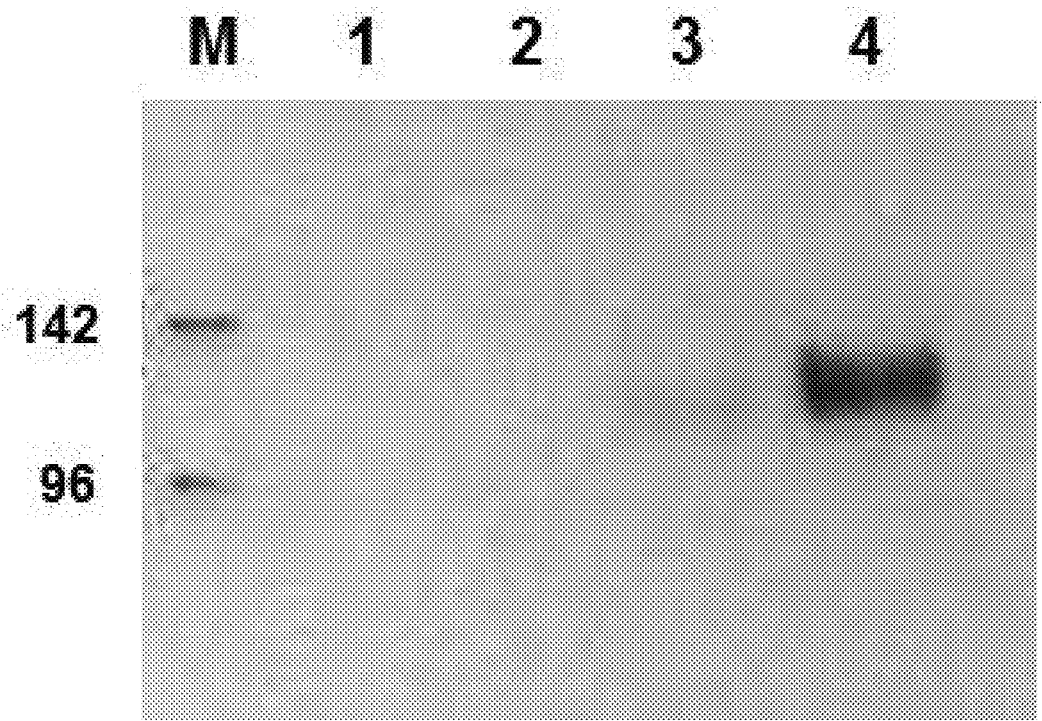
FIG. 7 is a blot view thereof.
Figure 10:
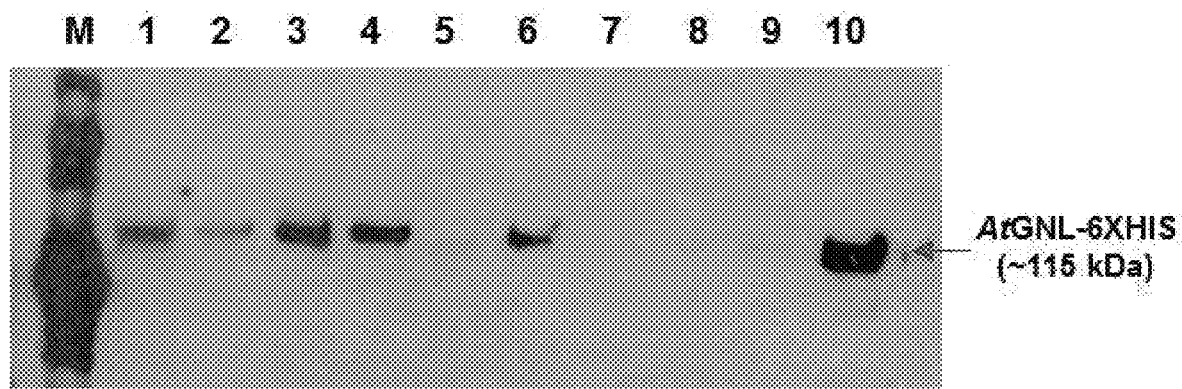
FIG. 10 is a blot view thereof.

Protein fractions from the various purification procedures were separated by SDS-PAGE and AtGNL was detected by Western blot. FIG. 10 shows the AtGNL protein extracted with different buffers. Western blot of total protein extracted from *N. benthamiana* leaves with different buffers as described in FIG. 7. M: marker, lane 1: crude extract with buffer-1, lane 2: crude extract with buffer-2, lane 3: crude extract with buffer-3, lane 4: crude extract with buffer-4, lane 5: crude extract with buffer-5, lane 6: sample extracted in buffer-5 and resuspended in buffer-4, lane 7: crude extract in buffer-5, lane 8: sample extracted in buffer-5 and resuspended in buffer-3, lane 9: sample extracted in buffer-5 and resuspended in buffer-6, lane 10: crude extract in buffer-6.

The optimal buffer to recover more recombinant protein was buffer 6.

Figure 11:
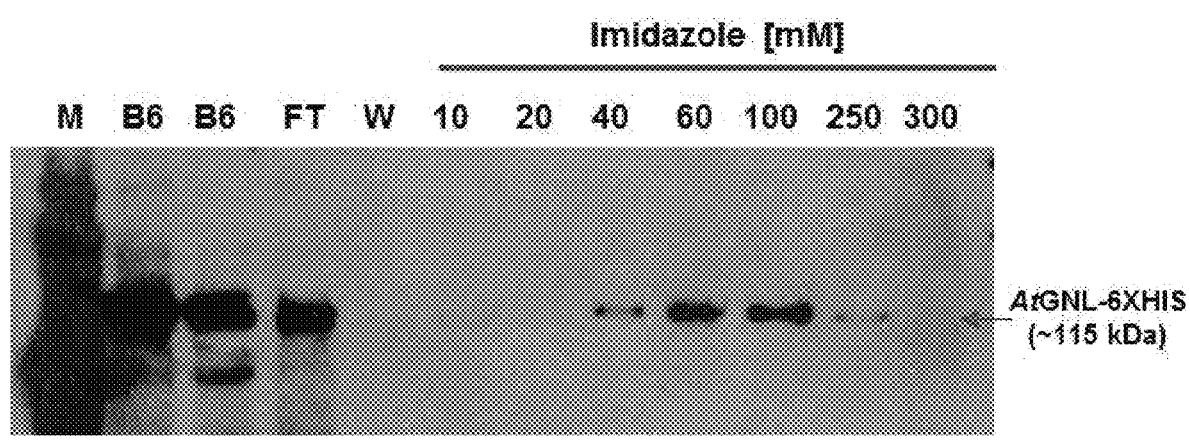
FIG. 11 is a blot view thereof.

In order to establish the optimal concentration for washing and elution buffer, several imidazole concentrations were tested. FIG. 11 shows the AtGNL protein eluted with different imidazole concentrations. Western blot of AtGNL protein with different concentration of imidazole. M: marker, B6: crude extract in buffer 6, FT flow through, W: wash buffer. As illustrated in FIG. 11, 40 mM and 250 mM were best for washing and eluting conditions, respectively.

FIG. 12 shows the Purification of the AtGNL:pBIB-kan-6×HIS expressed in *N. benthamiana* leaves. M: marker, lane 1: crude extract, lane 2: flow through, lane 3: wash, lane 4: enzyme, lane 5: concentrated enzyme. FIG. 12 illustrates the result of the purification of AtGNL from *N. benthamiana* tissue using nickel affinity chromatography. Western blot results showed the presence of AtGNL in the crude extract and flow through or wash indicating protein had a partial binding to the cation column. The silver-stained gel indicates that the protein preparation contained mostly the protein of interest with a few minor contaminants.

2.3.2. Enzyme Activity of Recombinant At1g56500

Once an effective purification procedure was developed, the next step was to standardize the assay to test the AtGNL activity. Gluconolactonase (GNL, EC 3.1.1.17) catalyzes the hydrolysis of D-glucono-σ-lactone (D-GulL) to D-gluconic acid (Ogawa et al., 2002). The lactonase activity was assayed in vitro based on the decrease in absorbance (405 nm) of the p-nitrophenol pH indicator that resulted from the enzymatic opening of the lactone ring when D-glucono-δ-lactone (D-GulL) was used as substrate in the presence of the AtGNL as previously described (Hucho and Wallenfels, 1972). The enzymatic activity was assayed at 25° C. with 10 mM PIPES pH 6.5, 5 mM D-GulL, 75 μM $MnCl_2$, 2.5 mM p-nitrophenol, and 30 μg of the purified enzyme (AtGNL) in 1 mL of reaction (Ishikawa et al., 2008). With the exception of D-GuTL, the recombinant AtGNL did not exhibit activity with any of the substrates tested. FIG. 13 shows the Substrate preference of AtGNL.

All enzymes work with a range of temperatures specific to the organism from which they are extracted. The effect of temperature on the AtGNL activity was also determined. The activity of the AtGNL enzyme was highest at temperatures between 25° C. and 35° C. The activity drastically decreased when the temperature was increased to 40° C. FIG. 14 shows the Effects of temperature and pH on the activity of the AtGNL enzyme. (A) pH effect on GNL activity. (B) Temperature effect on GNL activity. Measurements were made in duplicate. Values are means±SD. Ogawa et al., (2002) reported that the GNL enzyme from *A. niger* had higher activity at 30° C., while the activity of the GNL from *P. aeruginosa* is optimal at 24° C. (Tarighi et al., 2008), which are similar to the AtGNL.

Kondo et al., (2006), reported that the activity of the rat GNL was highest at pH 6.4, while Tarighi et al., (2008) demonstrated that the optimal activity of the *P. aeruginosa* GNL was at pH 7.2. In contrast, in this study the *A. thaliana* GNL enzyme had a higher activity at pH 6.0, and the activity decreased by 4-fold when the pH was increased to 6.3 (FIG. 14). Lower pH values were not tested because PIPES buffer cannot dissolve at pHs lower than 6.0.

To assess if the AtGNL activity had a preference for a particular divalent ion, various cofactors were tested. Ishikawa et al., (2008) reported that the GNL enzyme from *E. gracilis* had a higher activity using $ZnCl_2$ as a cofactor and that this activity decreased around 4-fold when changed to $MnCl_2$. In these experiments, no significant difference in GNL activity among the tested cofactors was observed (FIG. 15). Increasing the substrate concentration increased the rate of reaction or enzyme activity. In order to identify the optimal concentration of the D-glucono-δ-lactone, multiple substrate concentrations were tested. FIG. 15 shows the Effects of cofactor and substrate on the activity of the AtGNL enzyme. (A) Cofactors effect on GNL activity. (B) D-GuIL substrate concentration effect on GNL activity. Measurements were made in duplicate. Values are means±SD. The 3 mM of D-glucono-δ-lactone was the most effective substrate concentration for this assay.

Enzyme kinetic analysis was performed with D-GuIL at a concentration of 1 mM to 50 mM of substrate. The enzyme activity with 5 mM of D-GuIL at pH 6.0 was 10.54 μmol $min^{-1}$ $mg^{-1}$ of protein, $V_{max}=1.161\times10^{-6}$ (38.7 μmol $min^{-1}$ $mg^{-1}$ of protein) and $K_m=2.989$. FIG. 16 shows the Enzyme kinetics of the recombinant At1g56500 enzyme. (A) Michaelis-Menten. (B) Double reciprocal Lineweaver-Burke. Measurements were made in duplicate. Values are means±SD. FIG. 17 summarizes the comparison between the kinetic parameters of the AtGNL with the one of known GNLs. Based on these results the *G. oxidans* GNL is the most similar to the *Arabidopsis* GNL.

2.3.3. Characterization of the Phenotype of Gluconolactonase Lines with a Scanalyzer HTS Platform Seeds expressing the AtGNL-6×HIS:pBIB-kan (AtGNL) and empty pBIB-Kan (control) were screened in the Lorence Laboratory (unpublished). One hundred and thirty primary transformants that were PCR positive were screened to identify high AsA expressers. After four rounds of screening, three lines per group were selected for further analysis: over-expressers (WT+AtGNL), restored 1 (SALK_026172+ AtGNL), and restored 2 (SALK_011623+AtGNL).

Homozygous lines (T5), plants with 100% germination in the presence of antibiotic selection were developed for over-expresser (L60, L61, L62), restored-1 lines (L89, L90, L100), and restored-2 lines (L128, L129, L130). FIG. 18 shows the total foliar AsA level of AtGNL lines under normal light conditions. (A) Over-expressers and wild type (WT). (B) Restored lines and knockout control (S_026172). (C) Restored lines and knockout control (S_011623). Asterisks indicate significant differences between controls and high AsA lines as determine by Turkey multiple comparisons test, α=1, **=P<0.0001, *=P<0.0002, **=P<0.0017, *=P<0.0155. Values are means±SD, n=15.

The phenotype of these homozygous lines was analyzed using a Scanalyzer HTS instrument under normal conditions as described in materials and methods. Plant images were captured every two days from 16 to 26 days after germination. Representative images of homozygous AtGNL lines and their respective controls are shown in FIG. 19. From these images the projected leaf area as an indicator of plant growth was measured. FIG. 19 shows the Phenotype of AtGNL lines grown under normal conditions. (A) Representative images of AtGNL lines acquired with the visible camera (aka RGB). (B) Growth curves of AtGNL lines compared with their respective controls. Values are means±SE, n=15. There is a strong correlation between higher biomass and projected leaf area. Restored-1 and restored-2 lines had more biomass compared to their controls SALK_026172, SALK_011623, respectively, and those restored lines presented higher projected leaf area compared with their controls.

Based on these results, foliar AsA level, and the phenotype analysis, further studies were done only with the lines that had the highest foliar AsA content and fastest growth and higher biomass and projected leaf area.

Figure 20:
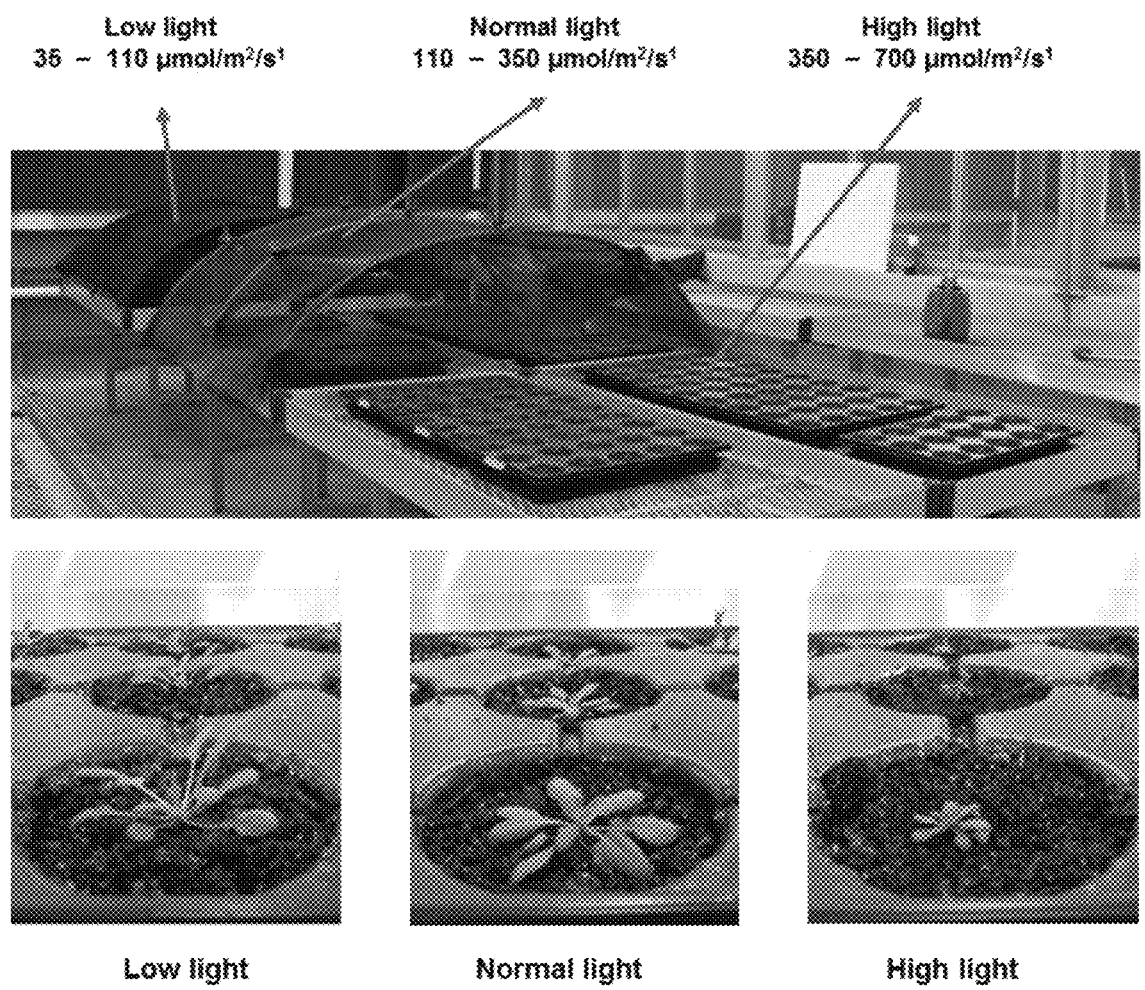
FIG. 20 is a photographic view thereof.

Over-expresser L61 (OE) and the empty vector control (EV); restored-1 L100 (R-1) and its control SALK_026172 (KO-1), restored-2 L129 (R-2), and its control SALK_011623 (KO-2), and wild type (WT) control were selected for further analysis. First, the effect of low and high light conditions on the selected plants was assessed. Routinely, plants are grown in environmental control chambers. A first attempt to study light effects was accomplished by growing plants in multiple chambers: (315=7 lines×15 biological replicates×3 light treatments). However, it was very difficult to achieve uniform conditions, with the only variable being the light intensity. To solve this problem, the experiment was conducted in the greenhouse. Two different density meshes were used to diffuse the light to the plants. FIG. 20 shows the experimental set up for studying the effect of light on the phenotype of AtGNL lines. Light intensity was measured four times per day (9:00 am, 12:00 pm. 3:00 pm, and 6:00 pm) to cover the sunlight period. The light intensity for these three treatment was defined as: low light (35-110 $\mu mol/m^2/s$), normal light (110-350 $\mu mol/m^2/s$), and high light (350-700 $\mu mol/m^2/s$).

Normal outdoor light on a sunny summer day is around 1000-2000 $\mu mol/m^2/s$ (Mishra et al., 2012) However, because *A. thaliana* is a spring understory plant, anything above 350 $\mu mol/m^2/s$ is considered high light.

Fifty mg of leaf tissue were collected at developmental stage 6.3 as defined by Boyes et al., (2001) between 9:00-11:00 am. Reduced, oxidized, and total AsA were measured via an enzyme-based method as previously described (Haroldsen et al., 2011). The results indicate that the over-expresser and the restored lines had a higher foliar AsA than their respective controls growing under similar conditions. FIG. 21 shows the Total foliar AsA levels of AtGNL lines under low, normal and high light conditions. (A) Over-expressers and wild type (WT). (B) Restored lines and knockout control (SALK_026172). (C) Restored lines and knockout control (SALK_011623). S026172 had a lower significant difference compared with wild type control at high light treatment. Each line was compared to the control (WT), analyzed by t-tests (LDS) at α=0.05. Significant differences are indicated by ***. WT: wild type, EV: empty vector, OE: over-expresser, KO: knockout, R: restored. n=15. The statistical analysis of total foliar AsA content in the three different light treatments in AtGNL lines shown in FIG. 22 validates this conclusion. Two-way ANOVA (α=0.05). The table in FIG. 22 indicates lines are significantly different and that there is a significant interaction between the lines and light treatments.

The projected leaf area results showed the same trend, where over-expressers and restored lines were bigger than their controls, with KO-1 being the worst performer at all light conditions tested. FIG. 23 shows the Projected leaf area of AtGNL lines grown under low, normal, high light conditions. (A) Low light. (B) Normal light. (C) High light. Values are means of 15 biological replicates. WT: wild type, EV: empty vector, OE: over-expresser, KO: knockout, R: restored. n=15. There is a strong correlation between foliar AsA level and projected leaf area: over-expresser and restored lines had higher foliar AsA levels and higher projected leaf area compared with their respective controls.

Figure 24:
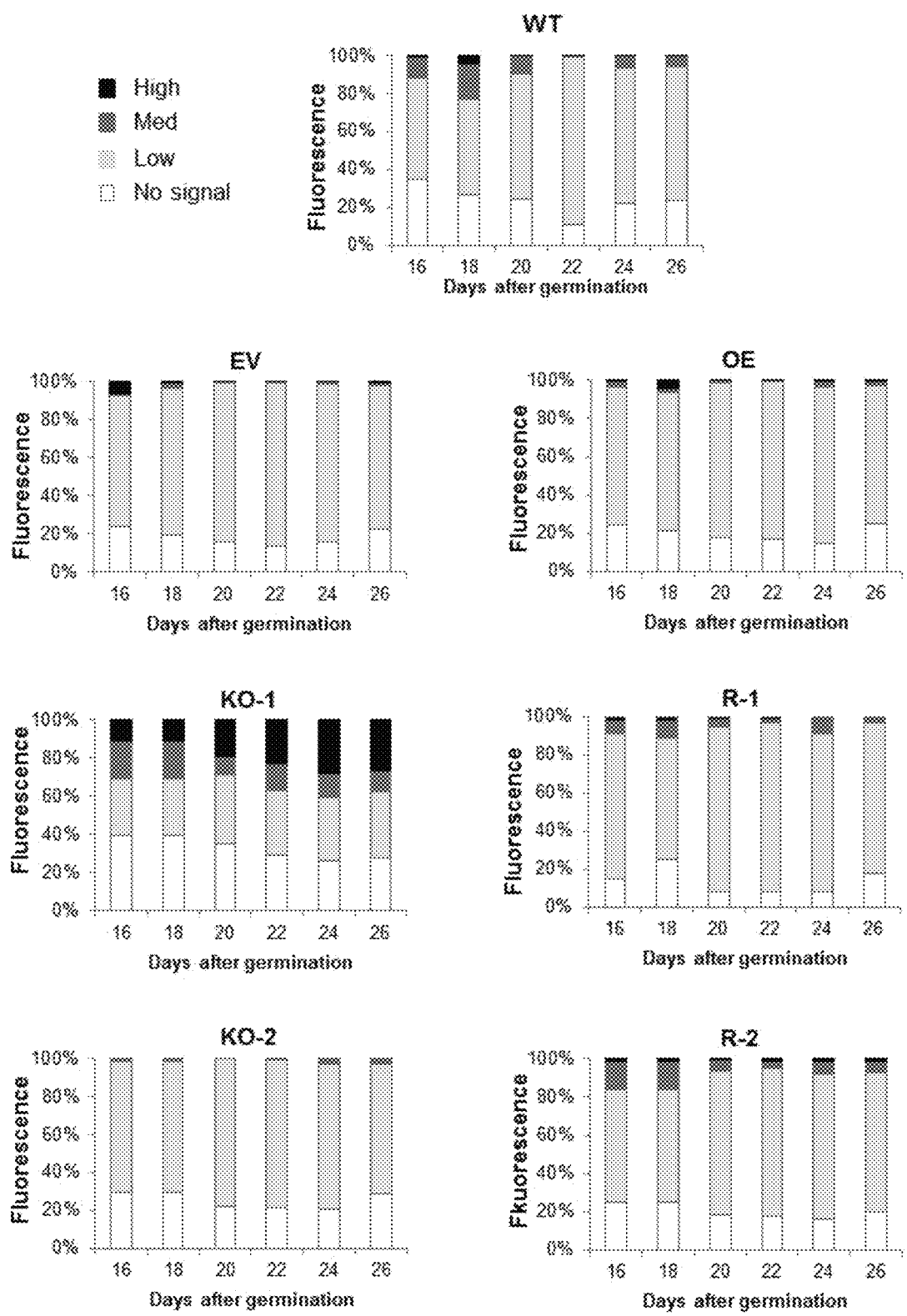
FIG. 24 is a chart view thereof.

In planta chlorophyll, fluorescence measured with the fluorescence camera can serve as an indicator of whether the plants are under stress. These plants were grown under the normal light regime. High fluorescence in plants is opposite of high photosynthetic efficiency (Lichtenthaler, 1988). FIG. 24 shows the Chlorophyll fluorescence patterns of AtGNL lines. Relative in planta chlorophyll content measured with the FLUO camera. Values are means of 15 biological replicates. WT: wild type, EV: empty vector, OE: over-expresser, KO: knockout, R: restored. n=15. The knockout KO-1 line showed high fluorescence compared to the other lines under high light conditions. This knockout line has a lower AsA level in the leaves, lower biomass, and projected leaf area, and also higher fluorescence compared with rest of the lines. Overall these results show that the AtGNL enzyme is essential to support normal AsA content in leaves and normal growth and development in *Arabidopsis*.

Figure 25:
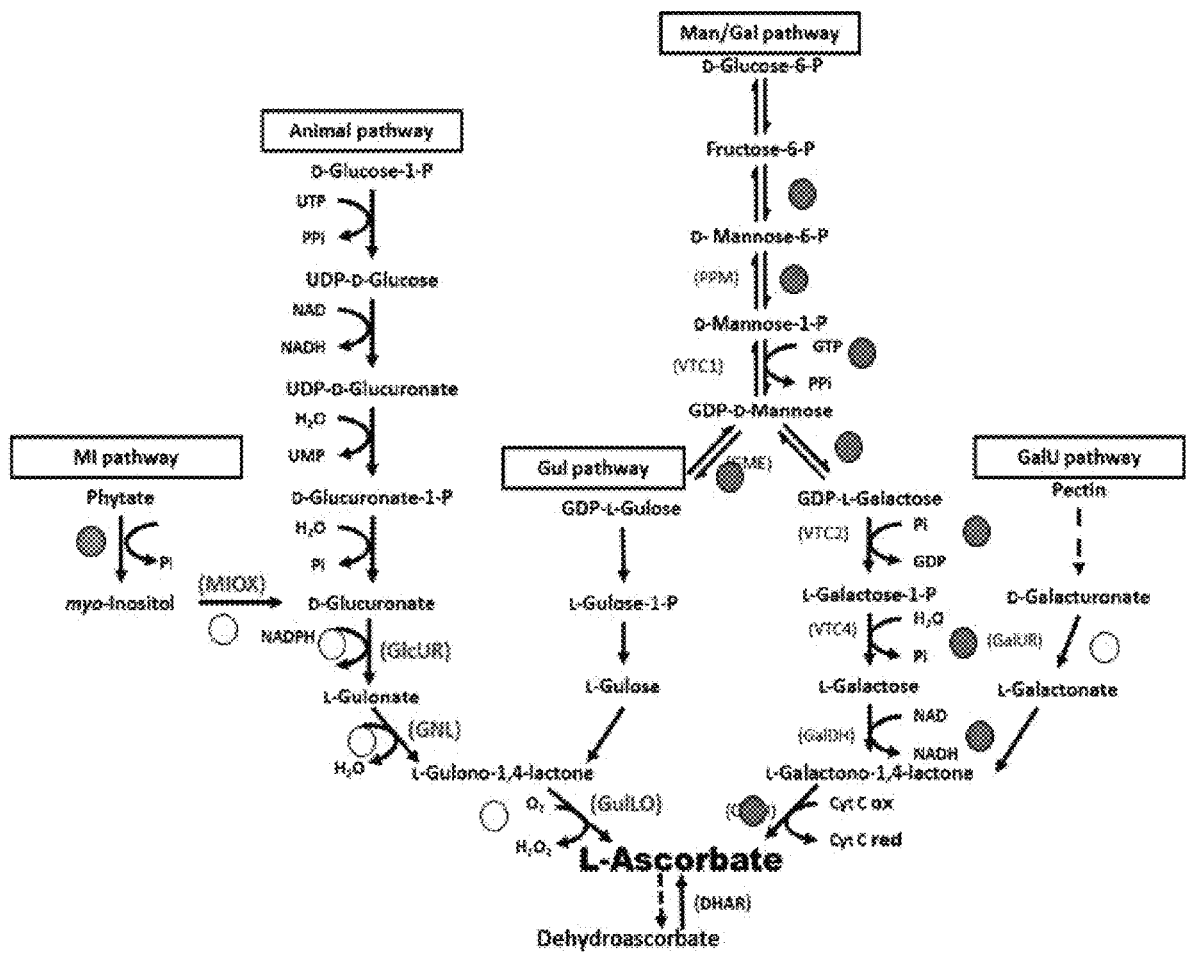
FIG. 25 is a metabolic network view thereof.

2.3.4. Photosynthetic Efficiency of AtGNL Lines Under Low and Normal Light Conditions Genes involved in the AsA metabolic network have been identified that were down and up regulated in response to light. FIG. 25 shows the Effect of darkness on the expression of genes in the AsA metabolic network. Microarray data deposited at Genevestigator was mined. Genes that are down regulated in darkness are shown in red, while genes that are up-regulated are shown in green. Yellow color indicates genes isoforms that are upregulated under dark conditions. The D-mannose/L-galactose, L-gulose and D-glucuronate pathway are repressed under low light conditions while the myo-inositol pathway keeps working. Suza and Lorence, unpublished. These results indicate that the L-gulose, D-mannose/L-galactose, and D-galacturonate pathways are down regulated under darkness, while the myo-inositol route is up regulated. If the transcripts are down regulated, the enzymes are expected to be down regulated as well. Because photosynthetic efficiency is a measure of light stress and redox potential, photosynthetic efficiency was analyzed for AtGNL lines growing under low and normal light conditions. These photosynthetic efficiency measurements were done with a MultispeQ, a hand-held device developed in the Kramer Laboratory (Michigan State).

Photosynthetic efficiency is the fraction of light (photons) that plants obtain from the sun to convert into chemical energy during photosynthesis. Under normal light conditions there was no penalty in the photosynthetic efficiency of plants lacking AtGNL expression. FIG. 26 shows the Photosynthetic efficiency of AtGNL lines under low and normal light conditions. Each line was compared to the control (WT), analyzed by t-tests (LDS) at α=0.05. Significant differences are indicated by ***. WT: wild type, EV: empty vector, OE: over-expresser, KO: knockout, R: restored. n=10. In contrast, the over-expressers and restored lines displayed enhanced efficiency indicating a positive impact on photosynthesis due to higher AtGNL expression. When plants were grown under low light, results were quite different. In this case a lower photosynthetic efficiency was detected in EV and KO-1 compared to the WT control. This indicates a penalty in photosynthetic efficiency due to lack of AtGNL expression. FIG. 27 shows the Statistical analysis of photosynthetic efficiency of AtGNL lines grew at low and normal light conditions. Two-way ANOVA (α=0.05). Photosynthetic efficiency as response to light conditions. The table indicates the treatment light has a significant effect pvalue=0.001. The lines also has a significant effect pvalue<0.0001, and there is a significant interaction between light and lines pvalue=0.1773.

In addition to photosynthetic efficiency two other parameters related to photosynthesis were measured: linear electron flow (LEF) and non-photochemical quenching (NPQt). The linear electron flow rate (LEF) has a direct correlation to photosynthetic efficiency. LEF facilitates the movement of $H^+$ ions across the thylakoid membrane to create an electrochemical gradient that is used by ATP-synthase to produce energy (ATP). FIG. 28 shows the Linear electron flow of AtGNL lines under low and normal light conditions. Each line was compared to the control (WT), analyzed by t-tests (LDS) at $\alpha=0.05$. Significant differences are indicated by ***. WT: wild type, EV: empty vector, OE: over-expresser, KO: knockout, R: restored. n=10. FIG. 28 shows that under low light conditions both knockouts had lower LEF values than the controls, while KO-1 was the line with the worst performance under normal light conditions. FIG. 29 shows the Statistical analysis of linear electron flow of AtGNL lines grown at low and normal light conditions. Two-way ANOVA ($\alpha=0.05$). LEF as response to light conditions. The table indicates the treatment light has a significant effect pvalue=0.0006. The lines also has a significant effect pvalue<0.0001, and there is a significant interaction between light and lines pvalue=0.0091. These data highlights the importance of the AtGNL enzyme for efficient ATP production in the chloroplasts.

Plants exhibit phenotypic plasticity and respond to differences in environmental conditions by acclimation. In a recent study, *Arabidopsis* plants grown under field conditions were compared with plants grown indoors. Indoor-grown plants had larger leaves, modified leaf shapes and longer petioles and less NPQt, while field-grown plants had a high capacity to perform state transitions (Mishra et al., 2012). If photosynthesis is inefficient, excess light energy is dissipated as heat to avoid damaging the photosynthetic apparatus. When plants are under abiotic stress, such as low light intensity, the photosynthetic efficiency and the NPQt are opposite. The KO-1 line had high NPQt, indicating inefficient photosynthesis at both low and normal light conditions. FIG. 30 shows the Non-photochemical quenching coefficient of AtGNL lines under low and normal light conditions. Each line was compared to the control (WT), analyzed by t-tests (LDS) at $\alpha=0.05$. Significant differences are indicated by ***. WT: wild type, EV: empty vector, OE: over-expresser, KO: knockout, R: restored. n=10. Statistical analysis indicates the KO-1 line had a highly significant difference compared to the WT control. FIG. 31 shows the Statistical analysis of non-photochemical quenching of AtGNL lines grown at low and normal light conditions. Two-way ANOVA ($\alpha=0.05$). Non-photochemical quenching as response to light conditions. The table indicates the treatment light has a significant effect pvalue=0.001. The lines also has a significant effect pvalue<0.0001, and there is a significant interaction between light and lines pvalue=0.4475. Overall, the over-expressers, restored lines, wild type, and empty vector lines had higher values of photosynthetic efficiency and LEF compared with KO lines under normal and low light conditions, while the NPQt values were opposite with the KO-1 having the highest value. These results show that AtGNL expression is essential to maintain high photosynthetic efficiency, high electron flow to make ATP (high LEF) and less loss of energy in the form of heat (NPQt).

2.3.5. Temporal and Spatial Expression of AtGNL Using the GUS Reporter Gene

To examine the expression of AtGNL within tissues, ten transgenic plants expressing GUS driven by the AtGNL promoter (pAt1g56500:pCAMBIA1305.1) and empty vector pCAMBIA1305.1 (control) were generated. In the empty vector the GUS-PLUS gene is under the control of the 35S constitutive promoter.

Figure 32:
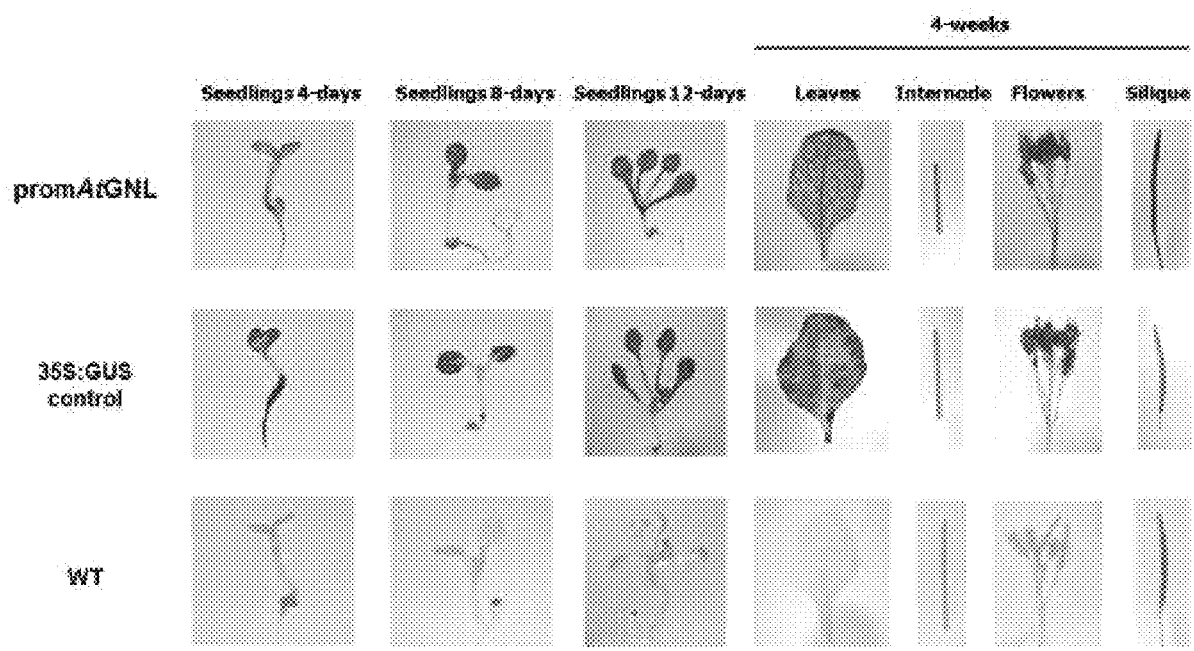
FIG. 32 is a photographic view thereof.

AtGNL, empty vector and wild type plants were treated with the X-Gluc substrate. As illustrated in FIG. 32 GUS activity was evident in plants expressing the AtGNL promoter in all developmental stages from cotyledons to roots, although much less staining was observed in 4-day-old seedlings compared with the controls. The oldest seedlings stained most intensely, especially at the leaf tips and margins. FIG. 32 shows the Temporal and spatial expression of AtGNL using the GUS-PLUS reporter gene. The AtGNL is expressed in the whole plant and at all developmental stages, indicating that the GNL enzyme is important in the physiological development of the plant from beginning to maturity.

2.3.6. Phylogenetic Three of Putative Plant Gluconolactonases

Figure 33:
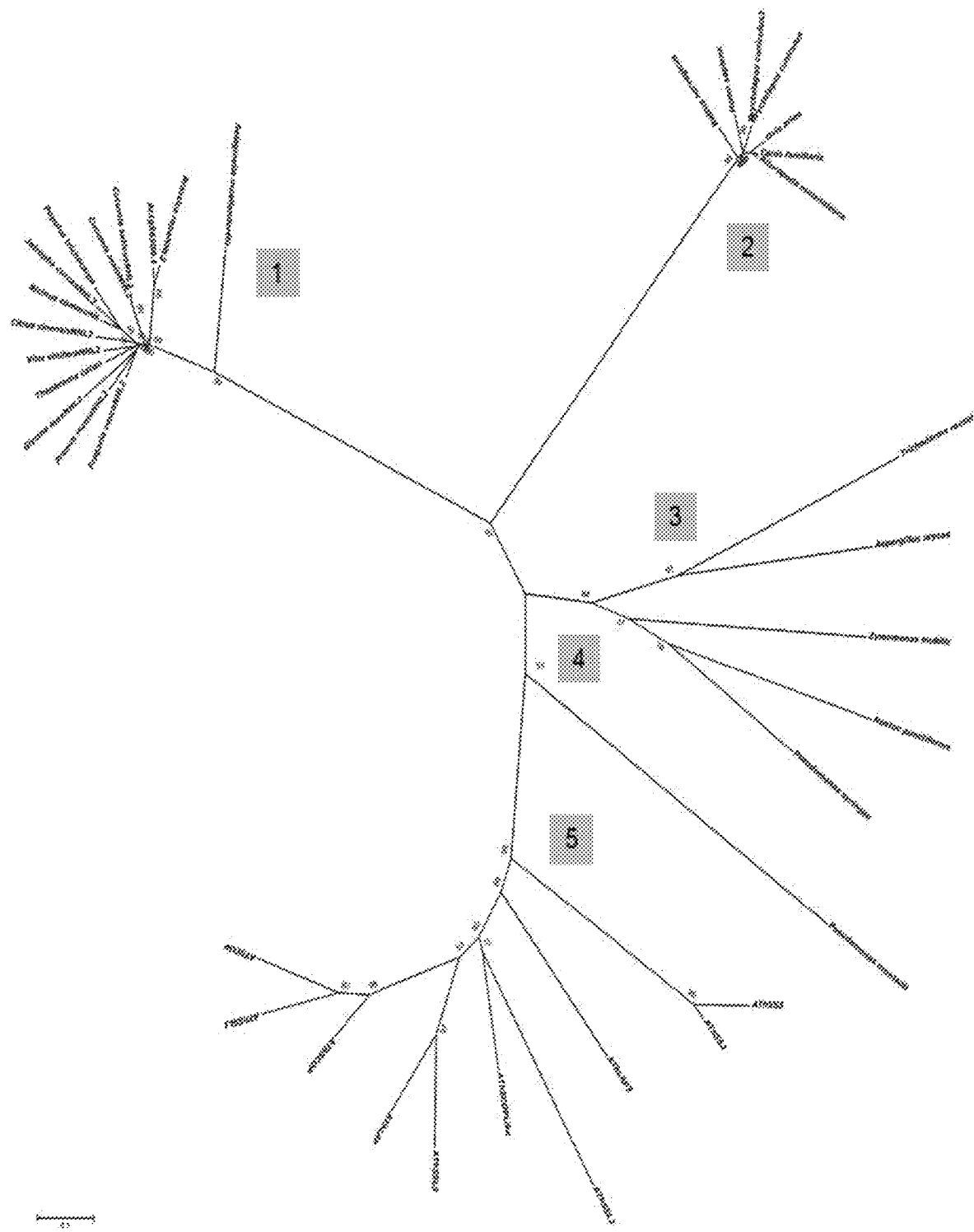
FIG. 33 is a phylogenetic view thereof.

A phylogenetic tree for At1g56500 (AtGNL) was generated. At1g56500 (AtGNL) was compared with known GNLs and with putative GNLs for many other organisms. After all protein sequences with significant sequence similarity to AtGNL were retrieved, the protein sequences were aligned using the MEGA6 software (Tamura et al., 2013). Only the sequences that had between 90 and 100% of identity with the AtGNL protein of interest were included in this analysis. To develop an updated phylogenetic tree, a BLASTP search was done against the *Arabidopsis* protein database (www.arabidopsis.org) using the *A. thaliana* gluconolactonase "At1g56500" (AtGNL) protein sequence. This enzyme has been characterized in *A. niger* (Ogawa et al., 2002), *E. gracillis* (Ishikawa et al., 2008), *P. aeruginosa* (Tarighi et al., 2008), *R. norvegicus* (Kondo et al., 2006), *Z. mobilis* (Pedruzzi et al., 2007), and now also in *Arabidopsis* (this work). The BLASTP result revealed the presence of 37 candidates in different organisms with 90-100% identity to the AtGNL query. FIG. 33 shows the Phylogenetic analysis of known and putative GNLs. Phylogenetic analyses were conducted in MEGA6 (Tamura et al., 2013). Five branches can be distinguished in this phylogenetic tree where the AtGNL groups with proteins from plant species including plant crops of agricultural importance including *Cucumis sativus* (cucumber), *Cucumis melo* (melon), *Citrus sinensis* (orange), *Vitis vinifera* (grapes), *Theobroma cacao* (cacao), *Glycine max* (soybean), and *Fragaria vesca* (strawberry), trees such as *Populus trichocarpa* (poplar) and *Prunus mume* (Chinese plum), and energy crops such as *Jatropha curcas*. The sequence similarity between At1g56500 and putative GNLs from other plants is remarkable. In a second group we can see known GNLs from mammalian species including *R. novergicus, H. sapiens*, and putative GNLs from *Ovis aries, Canis familiaris* and others. In the third and fourth branches we can see known and putative GNLs from bacteria and fungi. In a fifth group we find putative GNLs from *A. thaliana*. The analyses showed that At1g56500 has high similarity with the protein sequences listed in FIGS. 34A and 34B. FIGS. 34A and 34B show the List of known and putative GNLs included in the phylogenetic analysis. Underlined species indicate the GNL enzymes that have been characterized biochemically.

Figure 35:
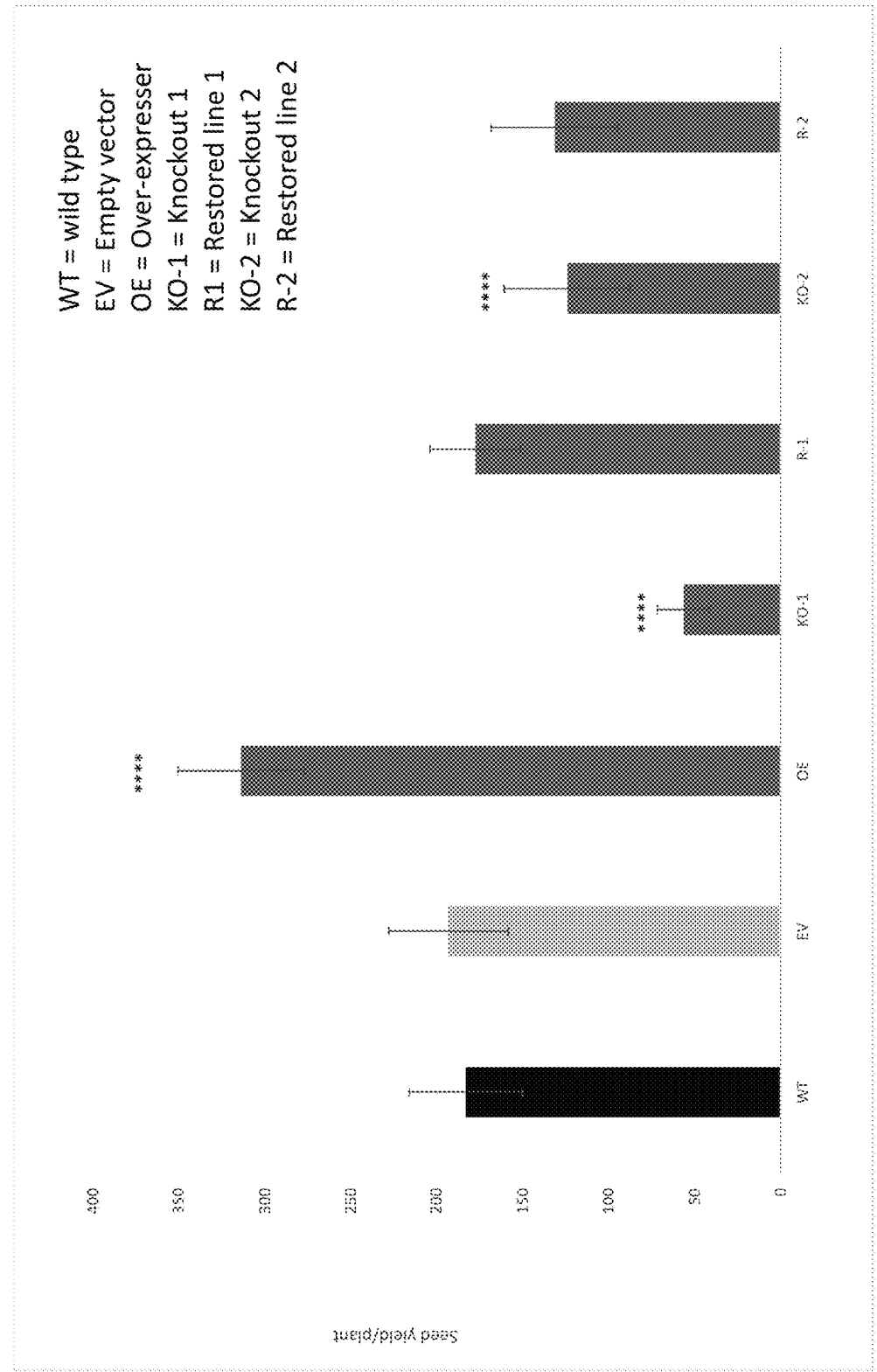
FIG. 35 is a chart view of one embodiment of the present invention.

The constitutive expression of the gene of interest (GNL) leads to higher seed yield in plants, such as *Arabidopsis*. Such higher seed yield is shown in FIG. 35.

FIGS. 36A, 36B, and 36C show the GNL DNA sequence.

FIG. 37 shows the GNL amino acid sequence. In one embodiment, the GNL over-expressed in the plant may include at least 70% of the sequence shown in FIG. 36 or FIG. 37.

2.4. Conclusions

The evidence presented in this document allows the following conclusions:

We successfully developed a purification protocol for AtGNL recombinant protein, and characterized this enzyme in detail including temperature, pH, cofactor requirement, and substrate concentration preferences, as well as its kinetic parameters.

The AtGNL enzyme had highest activity at temperatures between 25° C. to 35° C., while the bacteria *P. aeruginosa* has optimal temperature activity at 24° C. The optimum temperature of the AtGNL is consistent with the preferred growth temperature of *Arabidopsis*.

The optimal pH for AtGNL enzymatic activity was 6.0, and this activity decreased 4× when the pH was slightly increased (pH 6.3). In contrast, mammalian GNLs isolated from rats, mice, and humans have an optimal activity at pH 6.4. Our result is consistent with the prevalent pH in the chloroplasts (Alberts et al., 2002), the organelle where this protein resides.

The enzyme characterized in this work is very specific with the D-GuIL substrate. In contrast the recombinant GNLs from *E. gracilis* and *R. norvegicus* are promiscuous as they displayed activity with additional substrates (Kondo et al., 2006; Ishiwaka et al., 2008b).

GNL enzymes require a divalent cofactor for activity. The AtGNL displayed similar activity when incubated with $MnCl_2$, $MgCl_2$, or $ZnCl_2$. In contrast, other GNLs such as the *E. gracilis* isoform prefer $ZnCl_2$ and activity dropped significantly with other cofactors (Ishikawa et al., 2008). The ability of AtGNL to work with $MnCl_2$ is consistent with an enzyme that is active in the chloroplasts, as Mn is abundant in that organelle (Alberts et al., 2002).

Based on optimum pH, optimum T, and kinetic parameters of the known GNLs the one that is the most similar to the one here characterized is the *G. oxydans* GNL.

After demonstrating GNL enzyme activity in vitro, the present invention provides a method of controlling the role of this enzyme in AsA biosynthesis in planta. As shown in FIG. 18 when constitutively expressed in wild type, this enzyme leads to over-expressers with up to 3-fold increase in foliar AsA content. Two T-DNA insertion knockouts in this gene (SALK lines) had reduced AsA content compared to the WT control. When the functional gene was inserted into the knockout background this led to plants with restored AsA content. Overall this data indicates that AtGNL is functional in planta.

Previous results in the Lorence Laboratory obtained using manual phenotyping showed that plants with high AsA accumulate more biomass, delayed aging and are tolerant to abiotic stresses (Lisko et al., 2013). To determine if the AtGNL lines display differences in growth rate and biomass accumulation, a powerful high throughput phenotyping instrument was used to characterize the phenotype of lines with normal (WT), low (knockouts) and high (over-expresser and restores lines) GNL expression. A clear penalty in the growth rate and biomass accumulation of the knockouts exists. The restored lines grew as well or better than the controls. This result indicates that AtGNL is key to the plant to support normal growth and development.

Based on the fact that AtGNL is a chloroplastic enzyme (FIG. 7), to gain insights about the physiological role of this protein in supporting the function of this organelle, the ability of plants with low, normal, and high AtGNL expression to adapt to light stress conditions was analyzed. It is well established that there is higher ROS production during low and high light exposure (Sharma et al., 2012). *Arabidopsis* over-expressers and restored lines where AtGNL expression is enhanced display higher AsA content compared to controls.

Detailed characterization of the phenotype of the AtGNL lines under normal, low and high light conditions showed that over-expressers and restored lines grew better and accumulated more biomass than their respective controls (FIG. 23). The line with the poorest performance was KO-1, the genotype with the lowest AsA content. Interestingly in planta chlorophyll fluorescence analysis show that KO-1 displayed high chlorophyll fluorescence, an indicator of stress. Further analysis will have to be done to determine why KO-1 has a stronger phenotype compared to KO-2.

Plant growth and yield depend on plants maintaining high photosynthetic efficiency. To determine if the stunted growth we measured in the knockouts is due to deficiencies in photosynthesis, measurements were done with a hand-held fluorometer. Interestingly, results show that over-expressers and restored lines displayed enhanced photosynthesis compared to controls, while KO-1 and KO-2 have decreased LEF and therefore decreased ability to make ATP. Overall KO-1 display the poorest performance for all photosynthetic parameters here measured including non-photochemical quenching.

In order to analyze the expression of the AtGNL in plants tissues we developed transgenic *A. thaliana* lines expressing the GUS-PLUS reporter gene under the control of the AtGNL promoter (pAtGNL). The results show that AtGNL is expressed in all tissues examined: seedlings, leaves, stems, and siliques, except roots. This expression pattern suggests that AtGNL is a constitutive enzyme.

AtGNL is an important enzyme to sustain sufficient AsA content and to maintain plant growth and efficient photosynthesis. In order to gain insights about the conservation of this enzyme in evolution, a phylogenetic tree of known and putative GNLs was developed (FIG. 33). At least 37 candidates with 90-100% sequence identity to the AtGNL at the amino acid level exist. This analysis indicates the presence of GNLs in a wide array of plants including crops of agricultural importance, mammals, bacteria, and fungi. Interestingly it appears to be a GNL in *Sellaginella moellendorffii*, an ancient vascular plant that is widely used as a model to study the evolution of plants as a whole (Banks et al., 2011).

From the foregoing, it will be seen that the present invention is one well adapted to obtain all the ends and objects herein set forth, together with other advantages which are inherent to the structure.

It will be understood that certain features and sub-combinations are of utility and may be employed without reference to other features and sub-combinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

What is claimed is:

1. A method for increasing seed yield in a plant comprising: expressing in a genetically engineered plant a polynucleotide encoding a gluconolactonase (GNL) polypeptide with at least 90% sequence identity to SEQ ID NO:2 operably linked to a heterologous promoter to produce a plant with increased seed yield relative to a GNL wild-type plant and increased GNL expression relative to a GNL wild-type plant wherein the GNL wild-type plant is characterized as having wild-type level expression of a wild-type GNL polypeptide with at least 90% sequence identity to SEQ ID NO:2.

2. The method of claim 1, wherein the promoter is a constitutive promoter.

3. The method of claim 2, wherein the promoter is cauliflower mosaic virus 35S promoter.

4. The method of claim 1, wherein the polynucleotide is operably linked to an enhancer.

5. The method of claim 4, wherein the enhancer is a tobacco etch virus enhancer.

6. The method of claim 1, wherein the GNL polypeptide comprises SEQ ID NO:2.

7. The method of claim 6, wherein the polynucleotide encoding the GNL polypeptide comprises SEQ ID NO:1.

8. The method of claim 1, wherein the plant is transformed with a construct comprising the polynucleotide encoding a polypeptide with at least 90% sequence identity to SEQ ID NO:2 operably linked to a heterologous promoter.

9. The method of claim 8, wherein the plant is transformed using *Agrobacterium*-mediated transformation.

10. A genetically engineered plant with increased seed yield and increased gluconolactonase (GNL) expression comprising a construct, the construct comprising a polynucleotide encoding a GNL polypeptide with at least 90% sequence identity to SEQ ID NO:2 operably linked to a heterologous promoter, wherein seed yield and GNL expression of the genetically engineered plant is increased relative to a GNL wild-type plant of the same species lacking the construct wherein the GNL wild-type plant is characterized as having wild-type level expression of a wild-type GNL polypeptide with at least 90% sequence identity to SEQ ID NO:2.

11. The genetically engineered plant of claim 10, wherein the construct additionally comprises an enhancer.

12. The genetically engineered plant of claim 11, wherein the enhancer is a tobacco etch virus enhancer.

13. The genetically engineered plant of claim 10, wherein the promoter is a constitutive promoter.

14. The genetically engineered plant of claim 13, wherein the promoter is cauliflower mosaic virus 35S promoter.

15. The genetically engineered plant of claim 10, wherein the GNL polypeptide comprises SEQ ID NO:2.

16. The genetically engineered plant of claim 15, wherein the polynucleotide encoding the GNL polypeptide comprises SEQ ID NO:1.

17. The genetically engineered plant of claim 10, wherein the GNL polypeptide with at least 90% sequence identity to SEQ ID NO:2 is targeted to the chloroplast.

18. A seed of the genetically engineered plant of claim 10, wherein the seed comprises the construct.

19. A method for producing the genetically engineered plant of claim 10 comprising
transforming a plant with the construct comprising a polynucleotide encoding a GNL polypeptide with at least 90% sequence identity to SEQ ID NO:2 operably linked to a heterologous promoter to produce the genetically engineered plant.

20. The method of claim 19, wherein the plant is transformed using *Agrobacterium*-mediated transformation.

\* \* \* \* \*